(12) United States Patent
Lafargue et al.

(10) Patent No.: US 11,135,319 B2
(45) Date of Patent: Oct. 5, 2021

(54) COMPOUNDS USEFUL AS IMAGING AGENTS OF HYPOXIA

(71) Applicants: CENTRE NATIONAL DE LA RECHERCHE SCIENTIFIQUE, Paris (FR); UNIVERSITE DE CAEN NORMANDIE, Caen (FR)

(72) Inventors: Anne-Elodie Lafargue, Troarn (FR); Cecile Perrio, Caen (FR)

(73) Assignee: CENTRE NATIONAL DE LA RECHERCHE SCIENTIFIQUE, Caen (FR)

( * ) Notice: Subject to any disclaimer, the term of this patent is extended or adjusted under 35 U.S.C. 154(b) by 0 days.

(21) Appl. No.: 16/628,288

(22) PCT Filed: Jul. 5, 2018

(86) PCT No.: PCT/EP2018/068303
§ 371 (c)(1),
(2) Date: Jan. 3, 2020

(87) PCT Pub. No.: WO2019/008119
PCT Pub. Date: Jan. 10, 2019

(65) Prior Publication Data
US 2020/0171178 A1 Jun. 4, 2020

(30) Foreign Application Priority Data
Jul. 5, 2017 (FR) ...................................... 1756329

(51) Int. Cl.
*A61K 51/04* (2006.01)
*C07D 403/06* (2006.01)
(52) U.S. Cl.
CPC ........ *A61K 51/0453* (2013.01); *C07D 403/06* (2013.01); *C07B 2200/05* (2013.01)
(58) Field of Classification Search
None
See application file for complete search history.

(56) References Cited

FOREIGN PATENT DOCUMENTS

| WO | WO 2008/124651 A1 | 10/2008 |
| WO | WO 2015/104589 A1 | 7/2015 |

OTHER PUBLICATIONS

International Search Report dated Aug. 6, 2018 issued in PCT/EP2018/068303.
Fleming, I N et al., "Imaging tumour hypoxia with positron emission tomography", British Journal of Cancer (Dec. 16, 2014), vol. 112, No. 2, pp. 238-250.
Youssif, Bahaa Gamal Mohamed et al., "Development of a Hypoxia-Selective Near-Infrared Fluorescent Probe for Non-invasive Tumor Imaging", Chern. Phann. Bull. (Jan. 1, 2012), vol. 60, No. 3, pp. 402-407.
Lopci, Egesta et al., "PET radiopharmaceuticals for imaging of tumor hypoxia: a review of the evidence", Am J Nucl Med Mol Imaging (2014), vol. 4, No. 4, pp. 365-384.
Peeters, Sarah G.J.A. et al., "A Comparative Study of the Hypoxia PET Tracers [18F]HX4, [18F]FAZA, and [18F] FMISO in a Preclinical Tumor Model", International Journal of Radiation Oncology Biology Physics (2015), vol. 91, No. 2, pp. 351-359.
Bonnet, Muriel et al., "Novel nitroimidazole alkylsulfonamides as hypoxic cell radiosensitisers", Bioorganic & Medicinal Chemistry (2014), vol. 22, pp. 2123-2132.
Hiraoka, Shuichi et al., "A Molecular Ball Bearing Mediated by Multiligand Exchange in Concert", Angew. Chem. Int. Ed. (2004), vol. 43, pp. 3814-3818.
Leventis, Nicholas et al., "Synthesis and Characterization of Ru(II) Tris(1, 10-phenanthroline)-Electron Acceptor Dyads Incorporating the 4-Benzoyl-N-methylpyridinium Cation or N-Benzyl-N-methyl Viologen. Improving the Dynamic Range, Sensitivity, and Response Time of Sol-Gel-Based Optical Oxygen Sensors", Chem. Mater. (2004), vol. 16, pp. 1493-1506.
Yang, Haijun et al., "General Copper-Catalyzed Transformations of Functional Groups from Arylboronic Acids in Water", Chem. Eur. J. (2011), vol. 17, pp. 5652-5660.

*Primary Examiner* — Joseph R Kosack
(74) *Attorney, Agent, or Firm* — Scully, Scott, Murphy & Presser, P.C.

(57) ABSTRACT

The application relates to a compound with the following formula (I):

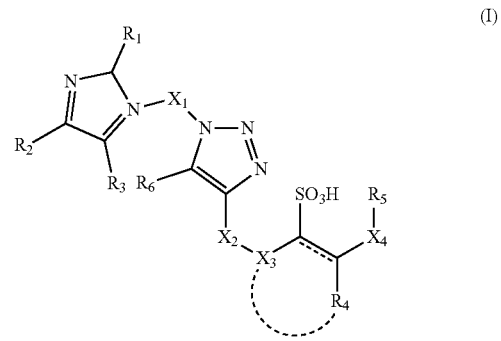

its preparation method, its synthesis intermediates and its uses as an imaging agent of hypoxia.

12 Claims, No Drawings

COMPOUNDS USEFUL AS IMAGING AGENTS OF HYPOXIA

The present invention relates to compounds useful as imaging agents of hypoxia, their methods of preparation, imaging methods implementing them and intermediate compounds useful for preparing them.

Hypoxia, namely a low concentration of oxygen, is associated with numerous pathologies, particularly ischemic cardiac diseases, vascular diseases, strokes and cancers. Within the scope of tumors, it is also considered to be the source of resistance to treatments, whether chemo- or radiotherapy.

Methods that are simple to implement and reproducible for detecting and quantifying hypoxia are therefore required for improving the care of patients, following the evolution of diseases and selecting the most suitable therapies.

Different techniques have been developed for this purpose. Among them, imaging methods by positron emissions tomography (PET) supply information on intracellular hypoxia are advantageously non-invasive and use imaging agents that inform directly regarding oxygen concentrations. Within this scope, Fleming et al. (*British Journal of Cancer*, 2015, 112, 238-250) and Lopci et al. (*Am. J; Nucl. Med. Mol. Imaging.*, 2014, 4(4), 365-384) describe imaging agents with the following formulas for detecting hypoxia using PET:

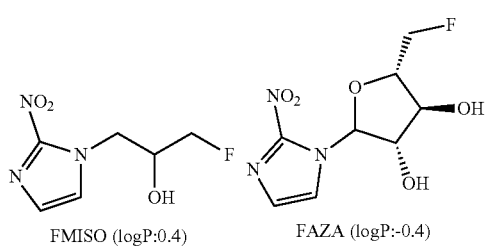

FMISO (logP:0.4)   FAZA (logP:-0.4)

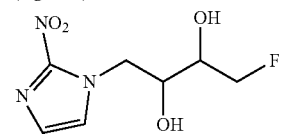

FETNIM (logP:-0.77)

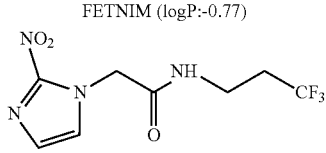

EF3 (logP:-0.05)

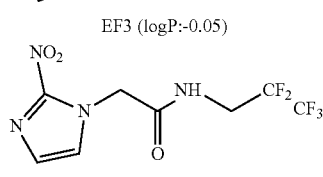

EF5 (logP:0.6)

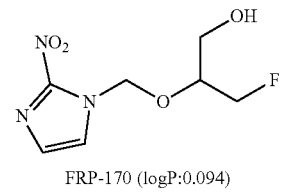

FRP-170 (logP:0.094)

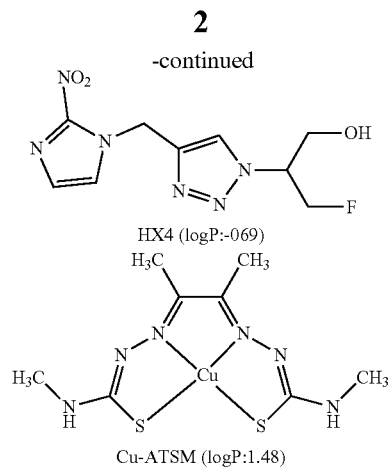

HX4 (logP:-069)

Cu-ATSM (logP:1.48)

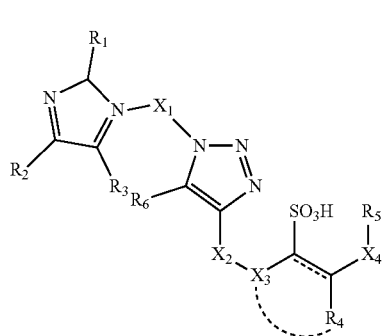

(I)

which can also be represented as:

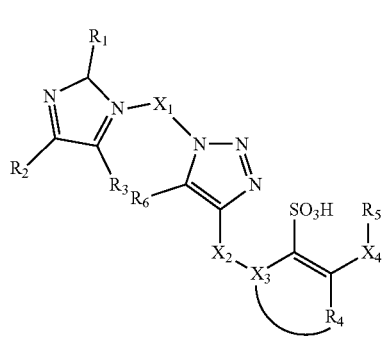

(I)

in which:

$R_1$, $R_2$ and $R_3$ independently represent —H, —$NO_2$, —$OR_{11}$ or a halogen, provided that at least one of $R_1$, $R_2$ or $R_3$ represents $NO_2$, $X_1$ represents an alkylene comprising from 1 to 4 carbon atoms, possibly interrupted by a group selected from —O—, —S—, —(C=O)—, —(CONR$_{14}$)—, —(NR$_{15}$CO)—, —NR$_{16}$R$_{17}$—, a cycloalkylene of 3 to 8 atoms and a heterocycloalkylene of 3 to 8 atoms, said cycloalkylene and heterocycloalkylene being possibly substituted by one or more groups selected from —S(O)$_m$R$_{18}$ where m represents an integer from 0 to 2, —R$_{19}$, —OR$_{20}$, —NR$_{21}$R$_{22}$ and a halogen, $X_2$ represents a single bond or an arylene comprising from 5 to 6 atoms, and possibly substituted by one or more groups selected from —COR$_{23}$, —COOR$_{24}$, —CONR$_{25}$R$_{26}$, —NR$_{27}$R$_{28}$, —S(O)$_p$R$_{29}$ where p represents an integer from 0 to 2, —R$_{30}$, —OR$_{31}$, a halogen, a cycloalkyl of 3 to 8 atoms and heterocycloalkyl of 3 to 8 members, said cycloalkylene and heterocycloalkylene possibly being substituted by one or more groups selected from the groups —S(O)$_q$R$_{41}$ where q represents an integer from 0 to 2, —R$_{42}$, —OR$_{43}$, —NR$_{44}$R$_{45}$ and a halogen, X$_3$ represents a multivalent hydrocarbon chain comprising from 1 to 6 carbon atoms, possibly interrupted by a group selected from —O—, —S—, —(C═O)—, —(CONR$_{32}$)—, —(NR$_{33}$CO)—, —NR$_{34}$R$_{35}$—, a cycloalkylene or heterocycloalkylene of 3 to 8 atoms, said cycloalkylene and heterocycloalkylene possibly being substituted by one or more groups selected among —S(O)nR$_{36}$ where n represents an integer from 0 to 2, —R$_{37}$, —OR$_{38}$, —NR$_{39}$R$_{40}$ and a halogen, R$_4$ represents —H, —OR$_{12}$ or a halogen, or R$_4$ and X$_3$ are bonded together to form a phenyl with the carbon atoms that carry them, X$_4$ represents —CR$_7$R$_8$— or —CR$_7$R$_8$—CR$_9$R$_{10}$—, R$_5$, R$_6$, R$_7$, R$_8$, R$_9$ and R$_{10}$ represent independently —H, —OR$_{13}$, a halogen or a radionuclide, provided that at least one of R$_5$, R$_6$, R$_7$, R$_8$, R$_9$ and R$_{10}$ represents a radionuclide, R$_{11}$, R$_{12}$, R$_{13}$, R$_{14}$, R$_{15}$, R$_{16}$, R$_{17}$, R$_{18}$, R$_{20}$, R$_{21}$, R$_{22}$, R$_{23}$, R$_{24}$, R$_{25}$, R$_{26}$, R$_{27}$, R$_{28}$, R$_{29}$, R$_{31}$, R$_{32}$, R$_{33}$, R$_{34}$, R$_{35}$, R$_{36}$, R$_{38}$, R$_{39}$, R$_{40}$, R$_{41}$, R$_{43}$, R$_{44}$ and R$_{45}$ represent independently H or a linear, branched or cyclic alkyl, comprising from 1 to 4 carbon atoms, R$_{19}$, R$_{30}$, R$_{37}$, and R$_{42}$ represent independently a linear, branched or cyclic alkyl comprising from 1 to 4 carbon atoms, or one of its pharmaceutically acceptable salts.

The compound with formula (I) comprises: at least one radionuclide (at least one of R$_5$, R$_6$, R$_7$, R$_8$, R$_9$ and R$_{10}$) which allows it to be detectable by positron emission tomography.

What is meant by radionuclide is an unstable isotope of an element, which can decompose while emitting radiation, in particular gamma radiation. Radionuclides or radioisotopes useful for implementing the invention are radionuclides of fluorine, iodine, astatine, carbon and/or the radiometals such as gallium, copper or lutetium. The radionuclide is preferably selected from among $^{120}$I, $^{123}$I, $^{124}$I, $^{125}$I, $^{131}$I, $^{76}$Br, $^{75}$Br, $^{18}$F, $^{211}$At, $^{11}$C, $^{13}$C, $^{14}$C, $^{99}$Tc and $^3$H, where $^{18}$F and $^{19}$F are particularly preferred.

According to embodiments particularly suitable for its implementation, the compound of formula I comprises from one to three radionuclides, in particular one or two and in particular only one. Advantageously, at least R$_5$ represents a radionuclide.

In addition, the compound with formula (I) comprises an imidazole and a —SO$_3$H group (possibly in the form of a pharmaceutically acceptable salt), which confer on it very hydrophilic properties (low log P).

Compounds with formula (I) can be in the form of pharmaceutically acceptable salts, for example those derived from ammonium salts, for example ammonium (NH$_4$$^+$), tromethamine, meglumine, or epolamine salts, or metal salts such as sodium, potassium, calcium, zinc or magnesium.

The "arylene comprising from 5 to 6 atoms" preferably comprises at least one carbon atom, the other atoms being selected among C, N, O and S. What can be cited for example are a phenylene, a furanylene, a thiophenylene, a pyrrolylene, an isoxazolylene, an isothiazolylene, an imidazolylene, a triazolylene, a pyridynylene or a pyrimidynylene.

A halogen is typically Cl, Br, I or F.

The linear, branched or cyclic alkyl comprising from 1 to 4 carbon atoms is for example a methyl, an ethyl, an n-propyl or s-propyl, a t-butyl or a cyclopropylmethyl, preferably a methyl.

In a preferred embodiment of the formula (I) above:

R$_1$, R$_2$ and R$_3$ represent independently —H, —NO$_2$, —OR$_{11}$ or a halogen, provided that at least one of R$_1$, R$_2$ or R$_3$ represents NO$_2$, X$_1$ represents an alkylene comprising from 1 to 4 carbon atoms, possibly interrupted by a group selected from among —O—, —S—, —NR$_{16}$R$_{17}$—, X$_2$ represents a single bond or an arylene comprising from 5 to 6 atoms, X$_3$ represents a multivalent hydrocarbon chain comprising from 1 to 3 carbon atoms, possibly interrupted by a group selected among —O—, —S— and —NR$_{34}$R$_{35}$ R$_4$ represents —H, —OR$_{12}$ or a halogen, or R$_4$ and X$_3$ are linked together to form a phenyl with the carbon atoms that carry them, X$_4$, R$_5$, R$_6$, R$_{11}$, R$_{12}$, R$_{16}$, R$_{17}$, R$_{34}$ and R$_{35}$ being as defined above.

The following embodiments, taken alone or in combination with one another, are particularly preferred in formula (I) or in the preferred embodiment of formula (I) described above:

R$_1$, R$_2$ and R$_3$ represent independently —H our —NO$_2$, provided that at least one of R$_1$, R$_2$ or R$_3$ represents NO$_2$, preferably R$_1$ represents NO$_2$ and R$_2$ and R$_3$ represent —H, and/or X$_1$ represents a group —(CH$_2$)$_n$—, or —(CH$_2$)$_p$—O—(CH$_2$)$_q$—, where n represents an integer from 1 to 4, preferably 1, and p and q represent independently 1 or 2, preferably 1, the group X$_1$═—CH$_2$— being particularly preferred, and/or R$_5$, R$_6$, R$_7$, R$_8$, R$_9$ and R$_{10}$ represent independently —H or a radionuclide, provided that at least one of R$_5$, R$_6$, R$_7$, R$_8$, R$_9$ and R$_{10}$ represents a radionuclide, preferably R$_1$ represents —H, and/or X$_2$ represents a single bond or a phenyl, and/or X$_3$ represents a multivalent hydrocarbon chain comprising from 1 to 3 carbon atoms, and/or R$_{11}$, R$_{12}$, R$_{13}$, R$_{14}$, R$_{15}$, R$_{16}$ and/or R$_{17}$ represent —H.

In one embodiment:

R$_1$ represents NO$_2$ and R$_2$, R$_3$ and R$_5$ represent —H, and X$_1$ represents a —CH$_2$— group, and the compound then has the following formula (II):

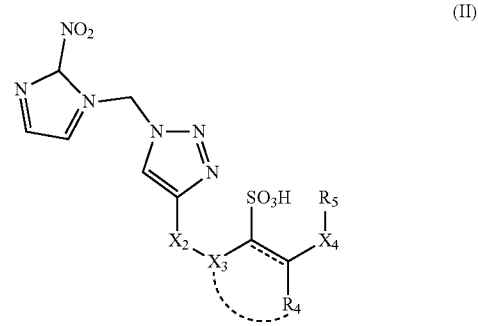

which can also be represented as:

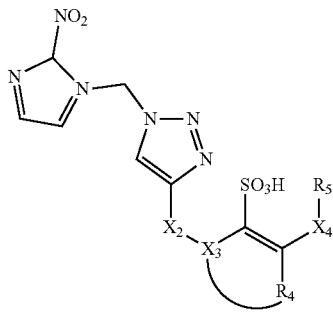

(II)

In which $X_2$, $X_3$, $X_4$, $R_4$, and $R_5$ are as defined above.
In the formulas of the present application,

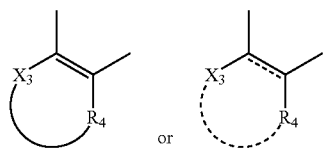

signify:
either that $X_3$ and $R_4$ are not bonded together. The bond between $CX_3$ and $CR_4$ is single.
This group then represents

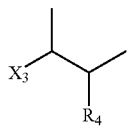

and the formula (I) reads:

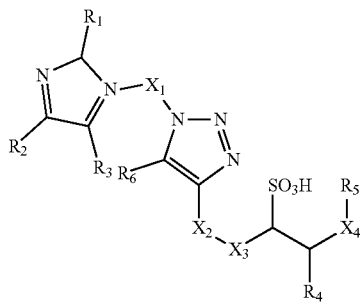

in which $X_1$, $X_2$, $X_3$, $X_4$, $R_1$, $R_2$, $R_3$, $R_4$, $R_5$, and $R_6$ are as defined above (the case of the first alternative detailed below),
or that $X_3$ and $R_4$ are bonded together to form a phenyl with the carbon atoms which carry them (the case of the second alternative detailed below).
According to a first alternative, in formulas (I) or (II), $X_3$ and $R_4$ are not bonded together. $R_4$ then represents —H, —OR$_{12}$ or a halogen, preferably —H. $X_3$ is then a divalent hydrocarbon chain comprising from 1 to 3 carbon atoms, possibly interrupted by an oxygen, a sulfur or an NR$_{16}$R$_{17}$ group. Preferably, $X_3$ represents —CH$_2$—. The compound typically has the following formula:

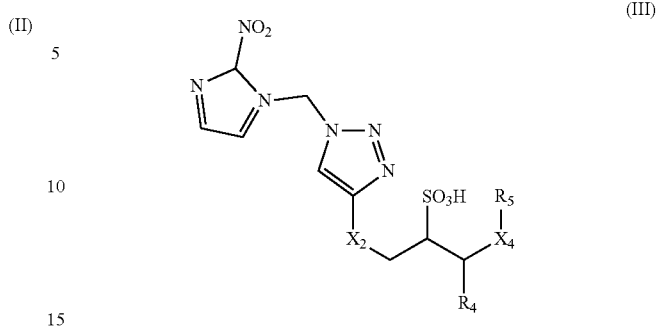

(III)

in which $X_2$, $X_4$, $R_4$, and $R_5$ are as defined above.
Preferably, in formula (III):
$X_2$ represents a single bond or a phenyl, and/or
$R_4$ represents H, and/or
$X_4$ represents —CH$_2$— or —CH$_2$—CH$_2$— and $R_5$ represents a radionuclide, preferably $^{18}$F.

For example, the compound has one of the following formulas (IIIa), (IIIb), (IIIc) or (IIId):

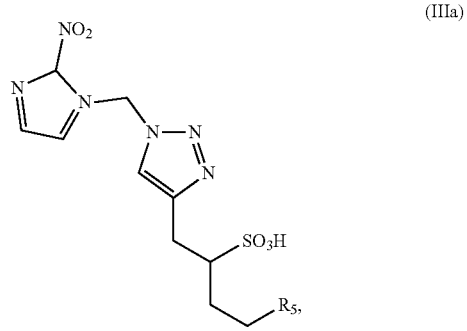

(IIIa)

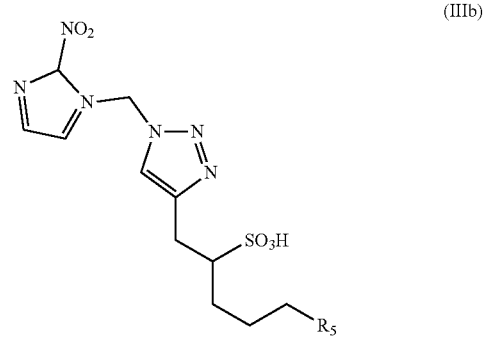

(IIIb)

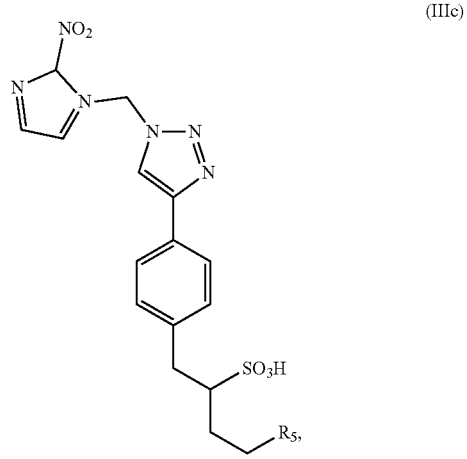

(IIIc)

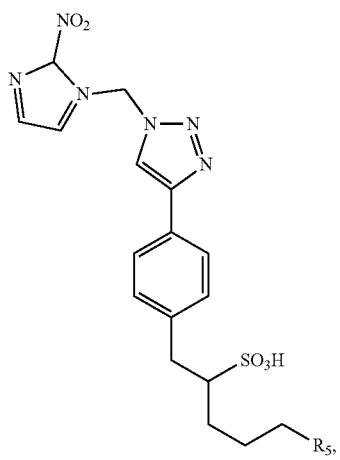

(IIId)

in which R$_5$ is a radionuclide, preferably $^{18}$F.

According to a second alternative, in formulas (I) or (II), X$_3$ and R$_4$ are bonded together to form a phenyl with the carbon atoms which carry them. X$_3$ then represents an uninterrupted multivalent hydrocarbon chain comprising from 1 to 3 carbon atoms. R$_4$ is then a hydrocarbon chain comprising 1 to 3 carbon atoms bonded to X$_3$ (the number of carbon atoms of R$_4$ depends on the number of carbon atoms of X$_3$ and on which carbon of X$_3$ is bonded to R$_4$).

Preferably:

X$_2$ represents a single bond, and/or

X$_4$ represents —CH$_2$— and R$_5$ represents a radionuclide.

For example, X$_2$ represents a single bond, X$_4$ represents —CH$_2$—, X$_3$ represents a trivalent hydrocarbon chain comprising 3 carbon atoms (the 1$^{st}$ carbon being bonded both to the triazolyl group and to R$_4$, and the 3$^{rd}$ carbon being bonded to —C(SO$_3$H)—), and R$_4$ is =CH—, and the compound then has the following formula (IV):

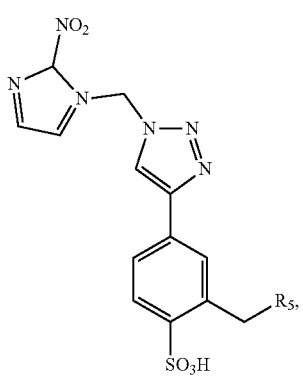

(IV)

in which R$_5$ is a radionuclide, preferably $^{18}$F.

According to a second object, the invention relates to the method for preparing the compound with formula (I) as defined above.

Two alternatives are possible for preparing the compound with formula (I).

According to a first alternative (alternative 1), the method comprises a step b) consisting of reacting a radionuclide and a compound with the following formula (XI):

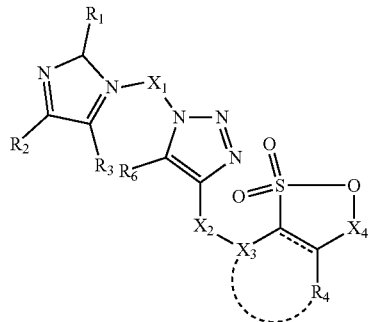

(XI)

which can also be represented as

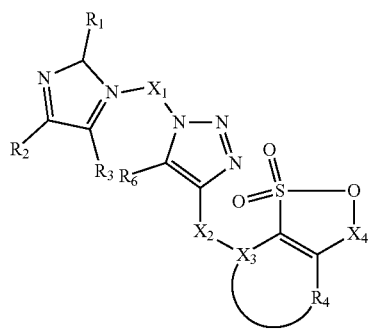

(XI)

in which R$_1$, R$_2$, R$_3$, X$_1$, X$_2$, X$_3$, X$_4$, R$_4$ and R$_5$ are as defined above.

Typically, the method comprises, prior to step b), a step a) consisting of preparation of the compound with formula (XI), comprising the reaction of a compound with the following formula (X):

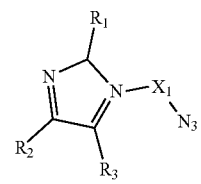

(X)

in which R$_1$, R$_2$, R$_3$, and X$_1$ are as defined above, with the compound having the following formula (XX):

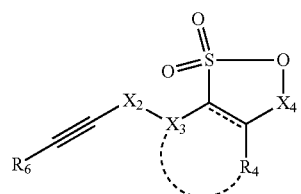

(XX)

which can also be represented as

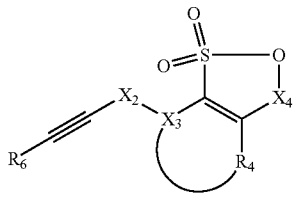
(XX)

in which $X_2$, $X_3$, $X_4$, $R_4$ and $R_6$ are as defined above.

According to a second alternative (alternative 2), the method comprises a step β) consisting of reaction of the compound with the following formula (X):

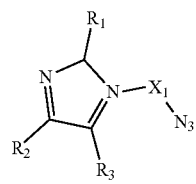
(X)

in which $R_1$, $R_2$, $R_3$, and $X_1$ are as defined above, with a compound having the following formula (XXI):

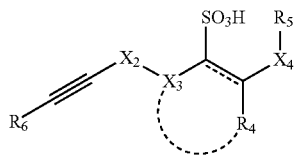
(XXI)

which can also be represented as

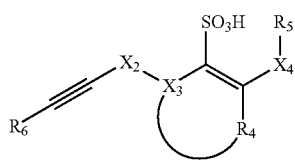
(XXI)

in which $X_2$, $X_3$, $X_4$, $R_4$, $R_5$ and RE are as defined above.

Typically, the method comprises, prior to step β), a step α) consisting of preparation of the compound with formula (XXI), comprising the reaction of a radionuclide with a compound with formula (XX) as defined above.

The two alternatives employ a compound with formula (XX), which can be prepared by methods known to a person skilled in the art, typically based on the corresponding sultone, which is deprotonated by a strong base (such as n-butyllithium) on the alpha carbon of the sultone, then contact with an electrophilic group allowing grafting of the $R_6C\equiv C-X_2-X_3$ group.

The following reaction scheme 1 illustrates the two paths for preparation of the compound with formula (I):

Reaction scheme 1: Synthesis paths for compounds with formula (I)

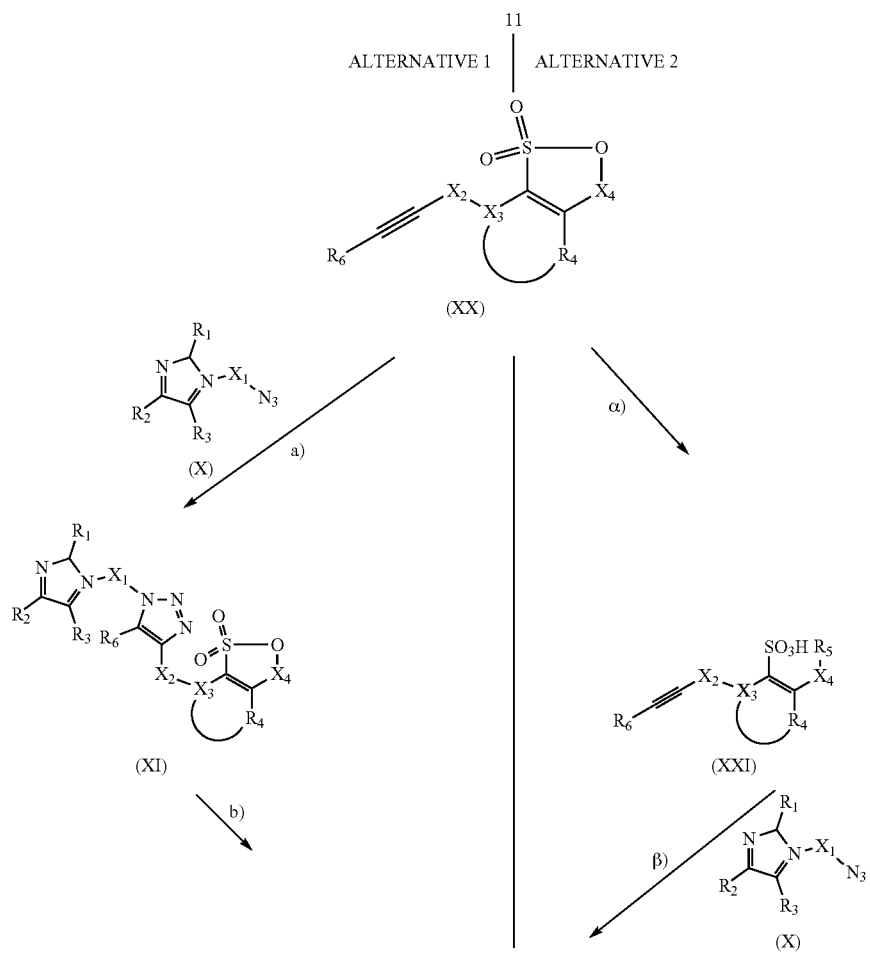

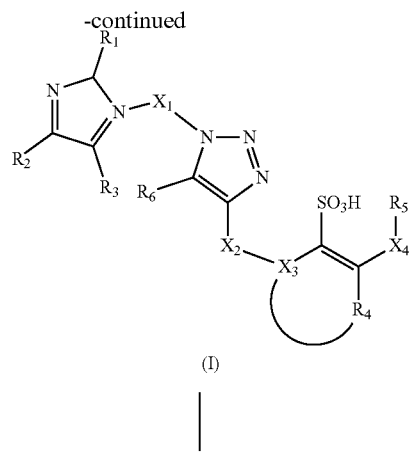

(I)

Reaction scheme 1: Synthesis Paths for Compounds with Formula (I)

Steps b) or α) lead to the opening of the sultone cycle by nucleophilic attack of the radionuclide, which is generally in the form of an anion. For example, when the radionuclide is $^{18}F$, these steps employ the $^{18}F^-$ anion, typically by using the fluoride [$^{18}F$] of tetra-n-butylammonium ([$^{18}F$]TBAF) or the complex [$^{18}F$] KF/K222 (Kryptofix 2.2.2). These steps b) or α) thus allow freeing the sulfonate function (possibly in the form of a salt) and introducing the radionuclide.

Regardless of the alternative of the method used, the method only implements a single step for introducing the radionuclide. The separation of the labeled compound (compound with formula (I) in alternative 1/compound with formula (XXI) in alternative 2) from its precursor (compound with formula (XI) in alternative 1/compound with formula (XX) in alternative 2) is very simple.

The preparation of compounds of formula (I) based on the sultone (XX) is therefore very easy, which advantageously allows compounds with formula (I) to be less costly. In particular, due to their very simple preparation method, the compounds with formula (I) are generally less costly than the imaging agents of the prior art described above. The simplicity of the method also makes it very easy to automate.

According to a third object, the invention relates to compounds with formula (XX), (XI) or (XXI) as defined above, in the form of a base or a salt. The compounds are useful as synthesis intermediates for compounds with formula (I).

The preferred embodiments describe above for formula (I) are of course applicable for compounds with formulas (XX), (XI) and (XXI).

In particular, among the compounds with formula (XI), those with formula (XII) are preferred:

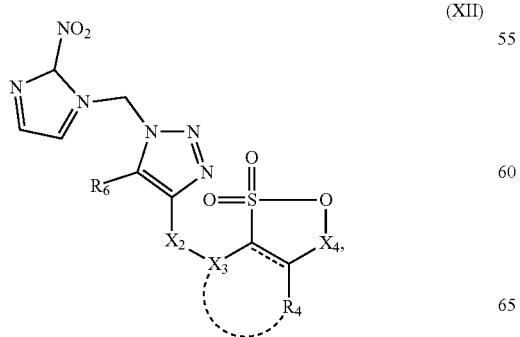

(XII)

which can also be represented as

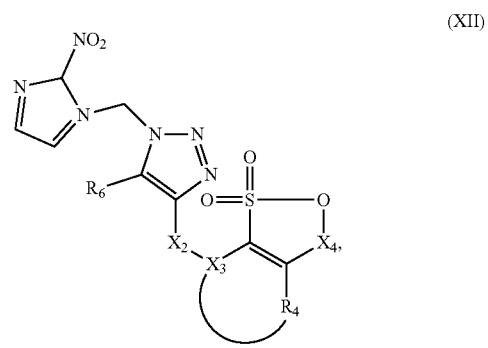

(XII)

in which $X_2$, $X_3$, $X_4$, $R_4$ and $R_6$ are as defined above, and in particular the following compounds with formulas (XIIIa), (XIIIb), (XIIIc), (XIIId) and (XIV):

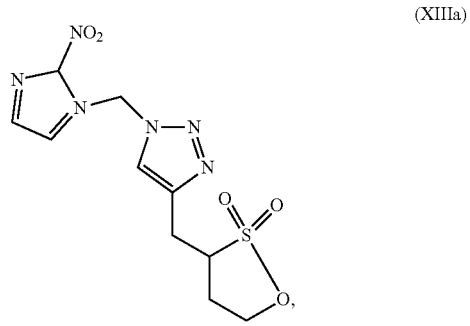

(XIIIa)

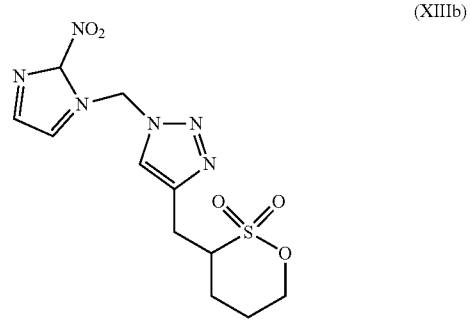

(XIIIb)

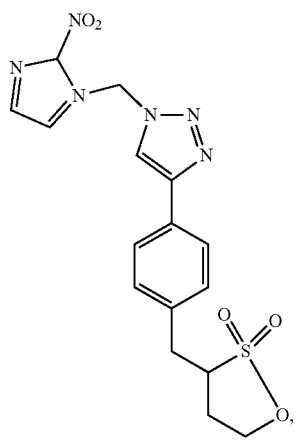
(XIIIc)

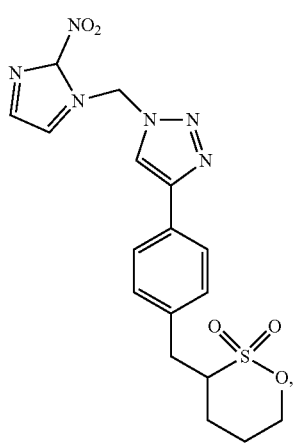
(XIIId)

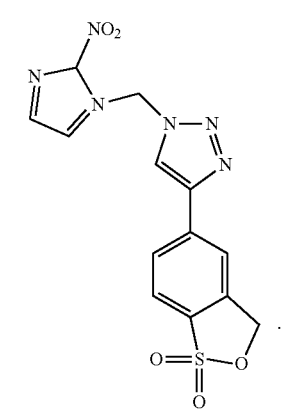
(XIV)

Among the compounds with formulas (XXI), the following compounds with formulas (XVIIIa), (XVIIIb), (XVIIIc), (XVIIId) or (XXIV) are preferred:

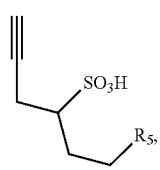
(XXIIIa)

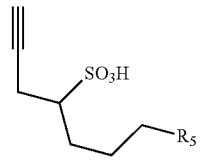
(XXIIIb)

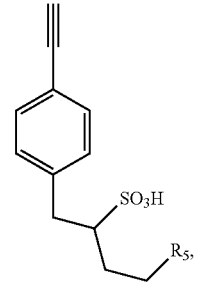
(XXIIIc)

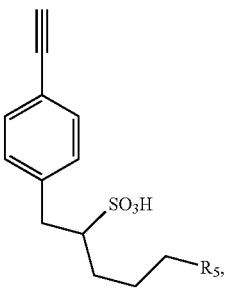
(XXIIId)

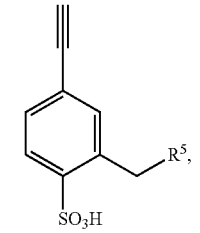
(XXIV)

in which $R_5$ is a radionuclide, preferable $^{18}F$. These compounds can be in the form of a salt, for example in the form of a pharmaceutically acceptable salt as defined above, but also in the form of a salt with a cation resulting from the reaction with the radionuclide during step b) or α), for example with tetra-n-butylammonium as the cation.

Among the compounds with formulas (XX), the following compounds with formulas 10, 10 nis, 11, 12 or 13 are preferred:

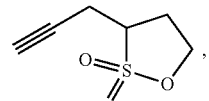
10

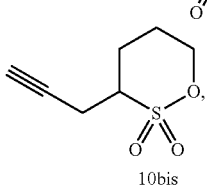
10bis

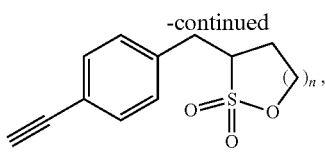

n = 1  11
n = 2  12

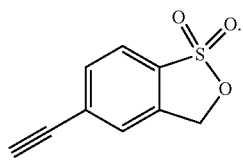

13

According to a fourth object, the invention relates to an imaging agent, particularly for PET, comprising the compound with formula (I) as defined above or one of its pharmaceutically acceptable salts. Due to its high affinity for water, the compound with formula (I) is very easy to formulate in a physiological medium. The imaging agent typically comprises the compound with formula (I) as defined above or one of its pharmaceutically acceptable salts, a pharmaceutically acceptable vehicle and a physiological medium.

The invention also relates to the use of a compound with formula (I) as defined above or of one of its pharmaceutically acceptable salts as an imaging agent, particularly for PET.

According to a fifth object, the invention relates to a compound with formula (I) as defined above or one of its pharmaceutically acceptable salts, intended to be used in an "in vivo" diagnostic method for hypoxia or a disease associated with hypoxia, such as cancer, a cardiac disease, a stroke or a cerebral vascular accident.

The invention relates in particular to compounds with formula I as defined in the present description and the examples, for their use in a diagnostic method for hypoxia, and more particularly as labelers of low or high hypoxia for cancers such as sarcomas, myelomas, lymphomas, cerebral tumors, head and/or neck tumors, tumors of the breast, of the lung, of ovaries, of the prostate or of the liver.

The invention also relates to a method for detecting hypoxia or a disease associated with hypoxia in cells comprising the steps consisting of:
  administration to a mammal, such as a human, of an effective quantity of a compound with formula (I) as defined above, then
  detection by positron emission tomography of the presence of the radionuclide in the hypoxic cells of the mammal.

The compound with formula (I) is particularly suited for intravenous administration.

It has, in the physiological condition, a high metabolic stability and very rapid pharmacokinetics. Its elimination through the kidneys and urine is quasi-exclusive, without capture by the digestive organs. The absence of competitive labeling of the digestive organs allows PET images to be obtained with a high signal-to-noise ratio and hence good contrast, which is not always the case with the imaging agents of the prior art described above.

The compounds with formula (I) are advantageously biocompatible and bioavailable. Without seeking to be linked to a particular theory, the inventors assume that the presence of the very hydrophilic imidazole and sulfonate groups is the source of these good properties.

Moreover, certain imaging agents of the prior art require post-injection delays of at least two hours to accomplish the imaging. However, certain pathologies, such as cerebral vascular accidents (CVA), require an accurate and precocious diagnosis or rapid care of the patient. The compounds with formula (I) are very advantageous in that they allow PET images to be accomplished right after injection. Typically, the signal originating in compounds with formula (I), is excellent starting 20 min. after injection, and remains optimum for at least 60 min. post-injection.

The following examples describe the preparation of certain compounds in conformity with the invention. These examples are not limiting, and only illustrate the present invention.

EXAMPLES

Reagents and Solvents

All the commercially available reagents were supplies by Sigma Aldrich, Alfa Aesar, Apollo Scientific and were used as received, without subsequent purification. The cRGD peptides were supplied by Peptides International, Human Serum Albumin was supplied by Sigma Aldrich and recombinant EPO (rhEPO) was supplied by Proteogenix.

The anhydrous THF, the diethyl ether and the dichloromethane (hereafter DCM) were obtained with the Mbraun SPS-800 solvent delivery system. The other anhydrous solvents were supplied by Sigma Aldrich. The HPLC and LCMS type solvents were supplied by Sigma Aldrich and the deuterated solvents were supplied by Euriso-top.

Spectroscopy

The RMN $^1$H (400 MHz), RMN $^{13}$C (100 MHz), RMN $^{19}$F (376 MHz) and RMN $^{11}$B (128 MHz) spectra were recorded on a Brücker DPX 400 apparatus and the RMN $^{15}$N (50 MHz) spectra on a Brücker Advance III 500 MHz. The samples were dissolved in an appropriate deuterated solvent (CDCl$_3$, CD$_3$CN, CD$_3$OD, D$_2$O or DMSO-d$_6$). Chemical shifts δ have been reported in parts per million (ppm) with reference to the proton resonances originating in the incomplete deuteration of the solvent RMN. Chemical shifts $^{11}$B have been reported with BF$_3$.Et$_2$O as the external standard and chemical shifts $^{15}$N have been reported with aqueous ammonia as the external reference. The coupling constants (J) are provided in Hertz (Hz). The abbreviations of the coupling constants are the following: s (singlet), bs (large singlet), d (doublet), t (triplet), q (quadruplet), qt (quintuplet), m (multiplet), dd (doublet of doublets), dt (doublet of triplets), etc. . . . . .

The infrared spectra (hereafter IR) have been recorded on a Thermo Scientific Nicolet 380 FT-IR ATR spectrometer. Only the selected absorptions have been reported (in cm$^{-1}$).

Mass Spectrometry

The GCMS analyses were recorded on a Varian GCMS Saturn 2000 spectrometer by electronic impact (EI) and were carried out with a BPX SGE column (0.25 mm×30 m, 0.25 μm) with, as a stationary phase: 5% phenyl and 95% dimethyl polysiloxane, as a gas vector: helium and the following gradient: 3 min at 50° C., then linear gradient of 50° C. to 250° C. at 15° C. min$^{-1}$ and 10 min at 250° C. at a flux of 1 mL·min$^{-1}$.

The high resolution mass spectra (HRMS) were obtained with a Waters Q-TOF micro-spectrometer using ionization by electro-nebulization (ESI). The relative intensities are given in brackets.

The LCMS analyses were carried out on an LC Waters Acquity UPLC apparatus equipped with a Waters Acquity UPLC BEH C18 inverse phase column (2.1×75 mm, 1.7 µm) with the following gradient: (A: MeOH, B: H$_2$O-0.1% formic acid) 0-20 min: linear gradient from 10% A to 90% A; 20-30 min: 10% A isocratic at 0.3 mL/min. The LC apparatus was coupled to an MS Waters Q-TOF electro-nebulization ionization micro-spectrometer. The source temperature was 300° C. and the analyses were carried out in the appropriate ionization mode (ES$_+$ ou ES$_-$) within the range of mass of 100 to 1500 Da. The LCMS conversions and quantifications were determined by calculating the ratio of the mass intensity between the desired compound and the initial product.

Fusion Point

The fusion points were determined on a Barnstead Electrothermal IA 9100 apparatus and were not corrected.

Elementary Analysis

The elementary analyses were carried out on a Thermo-Quest NA2500 CHNS apparatus and were in the range of ±0.4% relative to the calculated values.

Chromatography

Column chromatography was carried out on silica gel (Merck Kieselgel 60 F$_{254}$, 40-63 µm). Thin-layer chromatography (TLC) was carried out on Merck plastic plates covered with silica gel 60F$_{254}$. The spots were developed using a UV lamp at 254 nm and/or using vanillin, with KMnO$_4$ (for visualization of the sultone) or using ninhydrin. For the azide development, the plates were dried and immersed in a 10% triphenylphosphine solution in DCM, dried, immersed in a 0.3% ninhydrin solution in a mixture of ethanol/AcOH (100:3 v/v) and finally dried. The radioactive TLC was measured on a Packard Imager® device.

High performance liquid chromatography (HPLC) were carried out on a Waters 600 pump controller Waters 717 controller system plus autosampler and Water 996 photodiode detector (198-380 nm) coupled to a detector with an integrated NaI crystal radioactive source (Novolec β+-flow detector) or a Waters Alliance separation e2695 module, Waters 2998 photodiode detector (190-380 nm) and Berthold Herm LB 500 activity detector. The following chromatographic systems were used for the detection of products:

System A: analytical HPLC, Macherey-Nagel Nucleodur 100-3 Hilic, 150×4.6 mm, 3 µm, 1 mL/min Gradient 1: (A: acetonitrile (hereafter ACN), B: aqueous ammonium acetate 100 mM) 0-15 min: 3% B isocratic; 15-35 min: 3% B to 30% B linear increase; 35-40 min: 30% B isocratic.

Gradient 2: (A: ACN, B: aqueous ammonium acetate 100 mM) 0-3 min: 3% B isocratic; 3-5 min: 3% B to 50% B linear increase; 5-10 min: 50% B isocratic.

System B: analytical HPLC, Waters XTerra RP 18, 4.6× 250 mm, 5 lam, 1 mL/min

Gradient 1: (A: ACN, B: aqueous trifluoroacetic acid 0.1%) 0-5 min: 95% B isocratic; 5-7 min: 95% B to 60% B linear increase; 7-25 min: 60% B isocratic; 25-27 min: 60% to 20% B linear increase; 27-40 min: 20% B isocratic.

Gradient 2: (A: ACN, B: aqueous trifluoroacetic acid 0.1%) 0-4 min: 80% B isocratic; 4-15 min: 80% B to 10% B linear increase; 15-25 min: 10% B isocratic.

Gradient 3: (A: ACN, B: aqueous trifluoroacetic acid 0.1%) 0-10 min: 100% B isocratic; 10-15 min: 100% B to 60% B linear increase; 15-20 min: 60% B isocratic; 20-22 min: 60% to 20% B linear increase; 22-35 min: 20% B isocratic.

Gradient 4: (A: ACN, B: aqueous trifluoroacetic acid 0.1%) 0-15 min: 100% B isocratic; 15-20 min: 100% B to 60% B linear increase; 20-22 min: 60% B to 20% B linear increase; 22-35 min: 20% B isocratic.

Gradient 5: (A: ACN, B: aqueous trifluoroacetic acid 0.1%) 0-5 min: 100% B isocratic; 5-6 min: 60% B isocratic; 6-10 min: 20% B isocratic.

Gradient 6: (A: ACN, B: aqueous trifluoroacetic acid 0.1%) 0-10 min: 100% to 20% B linear increase.

System C: semi-preparative HPLC, Waters XTerra RP 18, 10×250 mm 10 µm, 5 mL/min

Gradient 1: (A: ACN, B: H$_2$O) 0-5 min: 100% B isocratic; 5-30 min: 20% B isocratic. UV detection λ=254 nm Gradient 2: (A: ACN, B: H$_2$O) 0-3 min: 100% B isocratic; 3-8 min: 80% B isocratic; 8-20 min: 20% B isocratic. UV detection h=316 nm Gradient 3: (A: EtOH, B: H$_2$O) 0-30 min: 90% B isocratic. UV detection A=316 nm Gradient 4: (A: ACN, B: aqueous trifluoroacetic acid 0.1%) 0-5 min: 100% B isocratic; 5-40 min: 100% B to 20% B linear increase; 40-45 min: 20% 5 B isocratic.

System D: analytical HPLC, Phenomenex BioSep-SEC-s2000, 7.8×300 with isocratic elution of 50 mM sodium phosphate and 300 mM NaCl, pH 6.8 (6.9 g of monobasic sodium phosphate monohydrate (NaH$_2$PO$_4$.H$_2$O) and 17.5 g NaCl in 900 mL H$_2$O adjusted to a pH of 6.8 with 50% NaOH and completed to 1000 mL with H$_2$O) at 1 mL/min.

The identity of the labeled compounds was determined by comparison with the unlabeled reference compound by HPLC or by radio-CCM.

Determination of the partition coefficient:

n-Octanol (1 mL) and H$_2$O (1 mL) were mixed for 20 min at ambient temperature before adding 10 µL of radioactively labeled compound. The tube was vigorously agitated by a vortex mixer for 30 min at ambient temperature. Three aliquots of 100 µL were collected from each phase and counted in a Packard Cobra Gamma counter. Log P was calculated as follows: log P=log (concentration of radioactivity in the n-octanol phase/concentration of radioactivity in the aqueous phase). The values provided are an average of the three measurements carried out.

In Vivo Imaging:

The evaluations of the radio-tracers were carried out in the animal rhabdomyosarcoma model provided by Biomedical Magnetic Resonance Research Group (REMA)—Catholic University of Louvain (UCL)—Belgium according to Peeters et al. (*Int J Radiat Oncol*, 2015) in the comparative study of [$^{18}$F]HX-4, [$^{18}$F]FMISO and [$^{18}$F]FAZA. The in vivo imaging was carried out using an Inveon µTEP/µTDM camera (Siemens). The animals were handled under gaseous anesthesia using isoflurane (induction at 5%, maintenance between 1.5% and 2.5% in 70% N$_2$O/30% O$_2$). The body temperature of the animals was maintained above 37.5° C. while the rate of respiration was constantly monitored, in order to obtain stable anesthesia reproducible from one animal to another. A catheter was placed without surgery (Insight Autoguard 24 Ga) at the caudal vein in order to allow the administration of radio-tracers. TDM acquisition is systematically performed prior to TEP imaging and is used for corrections of attenuation and diffusion of photos as well as for obtaining anatomical data. Acquisitions and reconstructions were performed with a coincidence time of 3.4 ns, an energy window of 350 to 650 keV, the OSEM3D-MAP reconstruction algorithm (respectively 2 and 18 iterations) with the "fastMAP" option, uniform variance and a required resolution of 2.26 mm. 128×128×159 pixels per image, with a voxel size of 0.776×0.776×0.796 mm$^3$. The images were normalized in SUV (Standardized Uptake Value) and analyzed with the PMOD (3.6 PMODTechnologies) software, by manual delimitation of the volumes of interest (VOIs) "entire tumor" and "muscle" and simultaneously using the 2 imaging modes.

Example 1: Preparation of a Compound with Formula (IIIb) with $R_5=^{18}F$ 1.1. Following the Method According to Alternative 1 (Steps a) and b) Described Above)

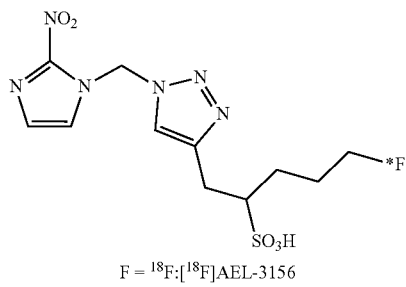

F = $^{18}$F:[$^{18}$F]AEL-3156

1) Synthesis of Precursors 2-4:

(DMSO-$d_6$, 400 MHz): δ 6.17 (s, 2H), 7.15 (d, $^3J$=1.0 Hz, 1H), 7.78 (d, $^3J$=1.0 Hz, 1H). RMN $^{13}$C (DMSO-$d_6$, 100 MHz): δ 55.2, 127.1, 127.9, 128.8. RMN 15N (DMSO-$d_6$, 50 MHz): δ 173.5, 271.5. HRMS (ESI+): calculated for $C_4H_4ClN_3NaO_2$: 184.9889 [M+Na]+; found: 185.1156

1-(Azidomethyl)-2-nitro-1H-imidazole 2 (Step b of Reaction Scheme 1)

(Compound Corresponding to Formula (X))

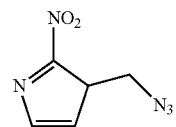

Formula: $C_4H_4N_6O_2$
Molecular weight: 168.11 g·mol$^{-1}$
Appearance: yellow solid To a solution of chloromethylnitroimidazole 1 (0.2 g, 1.2 mmol, 1 equiv) in $H_2O$ (10 mL) was added potassium iodide (0.1 g, 0.6 mmol, 0.5 equiv) and sodium nitride (234 mg, 3.6

Reaction scheme 1: synthesis path of compound 4 (compound corresponding to formula (XI)).

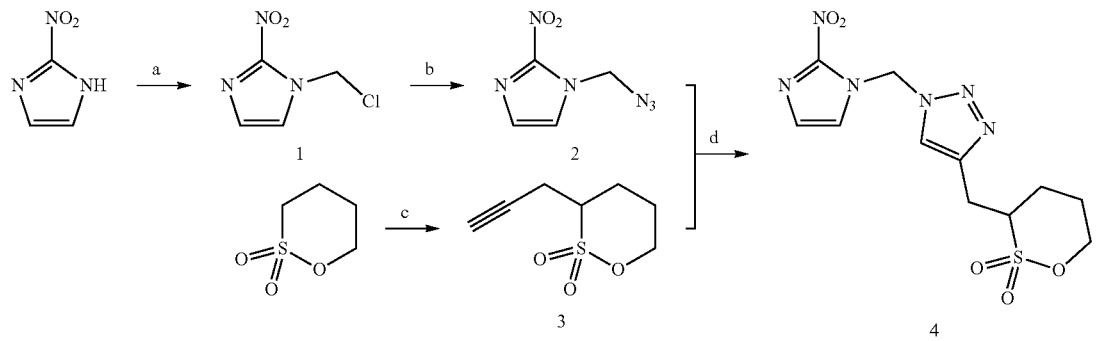

1-(Chloromethyl)-2-nitro-1H-imidazole 1 (Step a of Reaction Scheme 1)

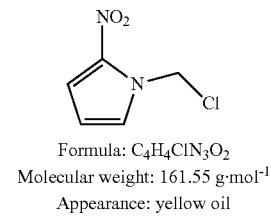

Formula: $C_4H_4ClN_3O_2$
Molecular weight: 161.55 g·mol$^{-1}$
Appearance: yellow oil To a solution of 2-nitroimidazole (0.2 mg, 1.77 mmol, 1 equiv) in anhydrous DMF (5 mL) were added bromochloromethane (2.3 mL, 35.4 mmol, 20 equiv) and cesium carbonate (1.15 g, 3.54 mmol, 2 equiv). The reaction medium was mixed at ambient temperature for 24 h and diluted in EtOAc and $H_2O$. The organic phase was washed with $H_2O$ and brine, dried over $MgSO_4$ and concentrated under reduced pressure, which led to the desired compound 1 appearing as a pale yellow oil, which was used without subsequent purification (236 mg, 81%).

CAS number: 1569296-82-7

Spectroscopic data agree with those described in Bonnet et al, *Bioorg Med Chem* 2014, 22 (7), 2123-2132. RMN $^1$H mmol, 3 equiv). The reaction medium was brought into reflux for 24 h and separated between EtOAc and $H_2O$. After separation, the organic phase was washed with $H_2O$ and brine, dried over $MgSO_4$ and concentrated under reduced pressure. Purification over silica gel with DCM/MeOH 1:0 to 9:1 as eluent led to the desired compound 2 appearing in the form of a yellow oil (0.19 g, 91%). pf: 52° C. $R_f$: 0.41 (DCM/MeOH 9:1). RMN $^1$H (DMSO-$d_5$, 400 MHz): δ 5.83 (s, 2H), 7.26 (d, $^3J$=1.0 Hz, 1H), 7.26 (d, $^3J$=1.0 Hz, 1H). RMN $^{13}$C (DMSO-$d_6$, 100 MHz): δ 62.6, 127.8, 128.6, 139.8. RMN $^{15}$N (CDCl$_3$, 50 MHz): δ 77.3, 173.5, 246.5, 270.6.

3-Prop-2-ynyl-[1,2]oxathiane 2,2-dioxide 3 (Step c of Reaction Scheme 1)

(Compound Corresponding to Formula (XX)

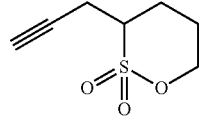

Formula: $C_7H_{10}O_3S$
Molecular weight: 174.22 g·mol$^{-1}$
Appearance: pale yellow solid In a double-necked flask under nitrogen were introduced 1,4-butanesultone (0.75 mL, 7.3 mmol, 1 equiv) and anhydrous THF (80 mL). The mixture was cooled to −78° C. and n-butyllithium (1.6M in hexane, 3.2 mL, 8.03 mmol, 1.1 equiv) was added drop by drop. The mixture was mixed at −78° C. for 15 min and propargyl bromide (0.81 mL, 7.3 mmol, 1 equiv) was added drop by drop. The mixture was mixed at −78° C. for 4 h, then allowed to gently reheat to 0° C., then treated with $H_2O$. After extraction with EtOAc, the combined organic phases were washed with $H_2O$, dried over $MgSO_4$ and concentrated under reduced pressure. Purification over silica gel with pentane/$Et_2O$ 1:1 as eluent led to the desired compound 3 in the form of a yellow oil (350 mg, 31%). pf: 66° C. $R_f$: 0.48 (Pentane/$Et_2O$ 1:1). RMN $^1H$ (CDCl$_3$, 400 MHz): δ 1.86-1.95 (m, 2H), 1.97-2.08 (m, 1H,), 2.10 (t, $^4J$=2.7 Hz, 1H), 2.42-2.48 (m, 1H), 2.53 (ddd, $^2J$=16.9 Hz, $^3J$=10 Hz, $^4J$=2.7 Hz, 1H), 2.93 (ddd, $^2J$=16.9 Hz, $^3J$=4.2 Hz, $^4J$=2.7 Hz, 1H), 4.48-4.53 (m, 2H). RMN $^{13}C$ (CDCl$_3$, 100 MHz): δ 18.4, 23.5, 27.5, 57.4, 71.9, 74.2, 78.0. HRMS (ESI+): calculated for $C_7H_{10}NaO_3S$: 197.0248 [M+Na]+; found: 197.0241.

3-((1-(2-Nitro-1H-imidazol-1-yl)methyl)-1H-1,2,3-triazol-4-yl)methyl)-1,2-oxathiane 2,2-dioxide 4 (Step d of the Reaction Scheme 1, which Corresponds to Step a) of the Method According to Alternative 1)

(Compound Corresponding to Formula (XI))

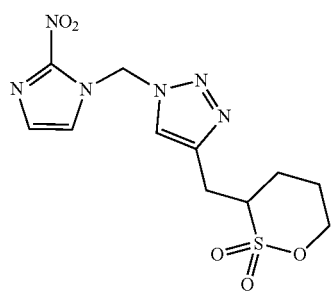

Formula: $C_{11}H_{14}N_6O_5S$
Molecular weight: 342.33 g·mol$^{-1}$
Appearance: white solid To a solution of azidoimidazole 2 (400 mg, 2.4 mmol, 1 equiv) in 1,4-dioxane (10 mL) were added acetylenic sultone 3 (415 mg, 2.4 mmol, 1 equiv), copper iodide (46 mg, 0.24 mmol, 0.1 equiv) and triethylamine (100 μL, 0.24 mmol, 0.1 equiv). The reaction medium was mixed at ambient temperature for 24 h, then separated between EtOAc and $H_2O$. After separation, the organic phase was washed with $H_2O$ and brine, dried over $MgSO_4$ and concentrated under reduced pressure. Purification on silica gel with DCM/MeOH 9:1 as eluent led to the desired compound 4 in the form of a white solid (680 mg, 84%). pf: 120° C. $R_f$: 0.43 (DCM/MeOH 9:1). RMN $^1H$ (CDCl$_3$, 400 MHz): δ 1.82-1.88 (m, 2H), 1.89-2.25 (m, 2H), 3.00 (dd, $^2J$=15.1 Hz, $^3J$=7.8 Hz, 1H), 3.40 (dd, $^2J$=15.1 Hz, $^3J$=5.8 Hz, 1H), 3.48-3.50 (m, 1H), 4.45-4.57 (m, 2H), 6.81-6.89 (m, 2H), 7.19 (s, 1H), 7.44 (s, 1H), 7.93 (s, 1H). RMN $^{13}C$ (CDCl$_3$, 100 MHz): δ 23.8, 24.9, 28.5, 58.8, 59.4, 74.0, 123.5, 126.2, 129.4, 143.6, 144.0. RMN $^{s1}N$ (CDCl$_3$, 50 MHz): δ 166.6, 240.5, 269.7, 359.1, 363.4. HRMS (ESI+): calculated for $C_{11}H_{15}N_6O_5S$: 343.0825 [M+H]+; found: 343.0825.

2) Synthesis of [$^{18}F$]AEL-3156:

Reaction scheme 2: synthesis path of the compound [$^{18}F$]AEL-3156 (compound corresponding to formula (IIIb) with $R_5$ = $^{18}F$).

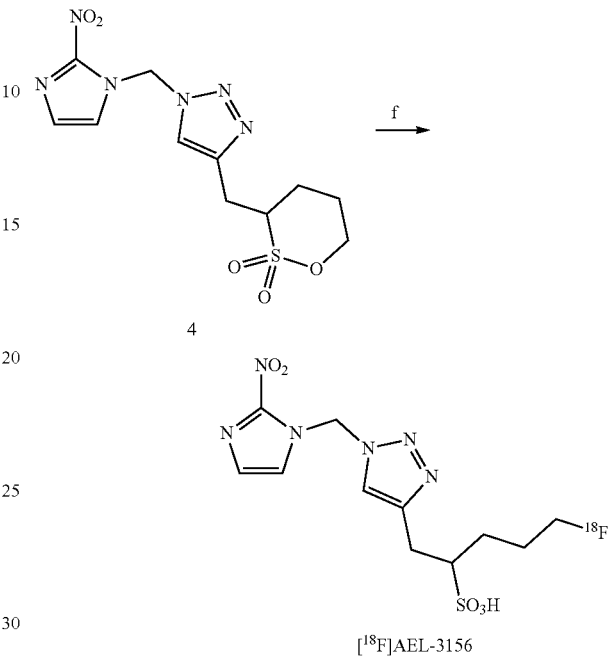

Single Step Radio-Synthesis of [$^{18}F$]AEL-3156 (Step f of Reaction Scheme 2, which Corresponds to Step b) of the Method According to Alternative 1)

The sultone precursor 4 (15 mg) in ACN (500 μL) has been added to the dried complex [$^{18}F$]KF/$K_{222}$ and the sealed reaction chamber has been heated to 110° C. for 15 min. Purification by HPLC has led to the desired compound with radiochemical efficiencies of 80-95%. HPLC: System B, gradient 3. [$^{18}F$]AEL-3156 ($t_R$=22.1 min), sultone precursor 4 ($t_R$=24.4 min).

1.2. Following the Method According to Alternative 2 (Steps α) and β) Described Above)

Reaction scheme 3: synthesis path of the compound [$^{18}F$]AEL-3156 (compound corresponding to formula (IIIb) with $R_5$ = $^{18}F$) by means of the compound [$^{18}F$]5 (compound corresponding to formula (XI)).

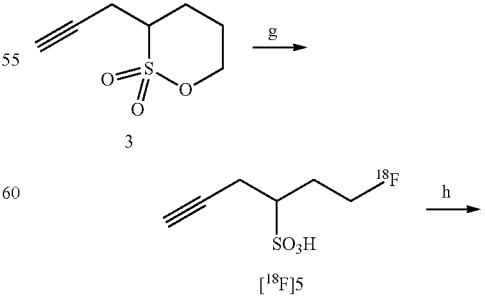

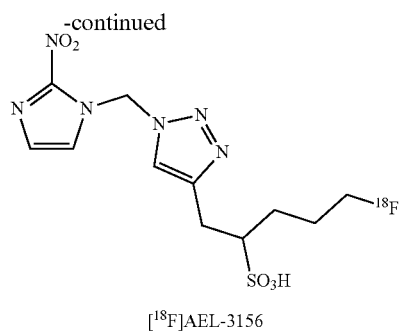

[¹⁸F]AEL-3156

Two-step radio-synthesis of [¹⁸F]AEL-3156 (steps g and h of the reaction scheme 3, which correspond to steps α) and β) of the method according to alternative 2)

Acetylenic sultone 3 (5 mg) in ACN (500 µL) was added to the dried complex [¹⁸F]KF/K$_{222}$ or to tetra-n-butylammonium fluoride [¹⁸F] (hereafter [¹⁸F]TBAF) and the sealed reaction chamber was heated to the desired temperature (ta, 50° C., 75° C. or 110° C.) for 15 min. ACN was eliminated at ambient temperature under a stream of nitrogen, which led to crude [¹⁸F]5, which was diluted in H$_2$O (0.5 mL). The solution was absorbed in a tC18 cartridge (Sep-Pak Plus®, Waters). The radioactive fraction was recovered with 1 mL of H$_2$O as eluent. ACN (2×500 µL) was added in order to eliminate water from [¹⁸F]5 azeotropically.

H$_2$O (500 µL), CuSO$_4$.TBTA (10 mM, 100 µL), sodium ascorbate (100 mM, 50 µL) and azidomethylnitroimidazole 2 (6 mg) were added to the dried [¹⁸F]5. The reaction medium was mixed at 90° C. for 30 min. Purification by HPLC led to the desired product [¹⁸F]AEL-3156 with radiochemical efficiencies of 75-85%. HPLC: System B, gradient 3. [¹⁸F]5 (t$_R$=7.6 min), [¹⁸F]AEL-3156 (t$_R$=22.1 min), sultone precursor 3 (t$_R$=20.5 min).

Log P value: −2.9

Example 2: Preparation of Compounds with Formula (XX)

2.1. Synthesis of Sultone 10:
(Compound Corresponding to Formula (XX))

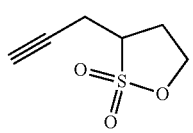

3-Prop-2-ynyl-[1,2]oxathiolane 2,2-dioxide 10

(Compound Corresponding to Formula (XI))

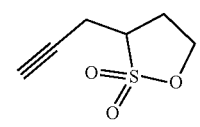

Formula: C$_6$H$_8$O$_2$S
Molecular weight: 160.19 g·mol⁻¹
Appearance: colorless oil HMDS (0.84 mL, 4.0 mmol, 1.7 equiv) and anhydrous THF (5 mL) were introduced into a double-necked flask (A) under nitrogen. After being cooled to 0° C., n-butyllithium (1.6M in hexane, 2.5 mL, 4.0 mmol, 1.7 equiv) was added drop by drop. The mixture was mixed at 0° C. for 15 min, then at −78° C. for 10 min. Propane-1,3-sultone (0.40 g, 3.3 mmol, 1.5 equiv), propargyl bromide (0.25 mL, 2.2 mmol, 1 equiv) and anhydrous THF (45 mL) were introduced into a second double-necked flask (B) under nitrogen. The mixture was cooled to −98° C. LiHMDS was transferred from flask A to flask B by a cannula and the final mixture was mixed at −98° C. for 4 h, allowed to reheat gently to 0° C. then treated with H$_2$O. After addition of EtOAc, the organic phase was washed with water, then with brine, dried over MgSO$_4$ and concentrated under reduced pressure. Purification on silica gel with pentane/Et$_2$O 1:1 as eluent led to the desired compound in the form of a colorless oil (112 mg, 32%). R$_f$: 0.31 (pentane/EtOAc 1:1). RMN ¹H (CDCl$_3$, 400 MHz): δ 2.14 (t, ⁴J$_{4-6}$=2.7 Hz, 1H), 2.45 (dq, ²J=13.6 Hz, ³J=8.0 Hz, 1H), 2.60 (ddd, ²J=17.2 Hz, ³J=8.8 Hz, ⁴J=2.8 Hz, 1H), 2.77 (ddd, ²J=13.6 Hz, ³J=8.0 Hz, ³J=5.6 Hz, 1H), 2.84 (ddd, ²J=17.2 Hz, ³J=5.8 Hz, ⁴J=2.6 Hz, 1H), 3.46 (dq, ³J=8.2 Hz, ³J=5.9 Hz, 1H), 4.35-4.49 (m, 2H). RMN ¹³C (CDCl$_3$, 100 MHz): δ 19.2, 28.9, 53.6, 66.7, 71.8, 77.3. HRMS (ESI+): calculated for C$_6$H$_9$O$_2$S: 161.0275 [M+H]+; found: 161.0272.

2.2. Synthesis of Aromatic Acetylenic Sultone Precursors 11-12

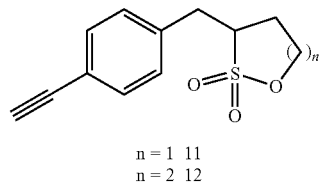

n = 1  11
n = 2  12

(Compound Corresponding to Formula (XX))
Reaction Scheme 4 was Followed

Reaction scheme 4: Synthesis path of sultones 11 and 12

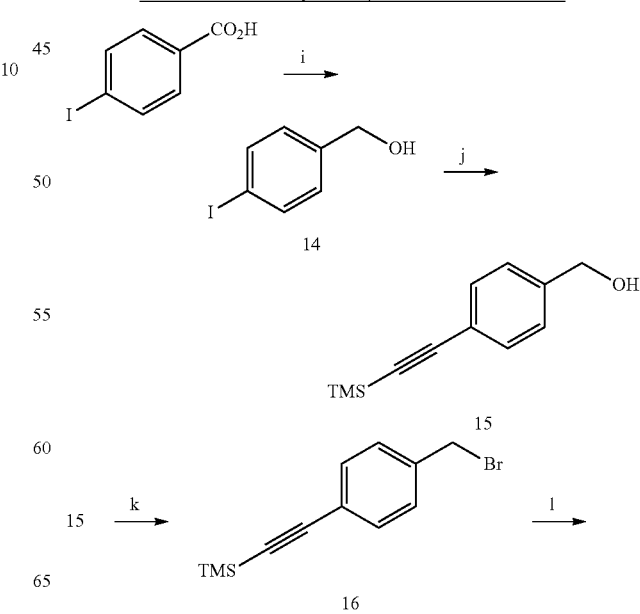

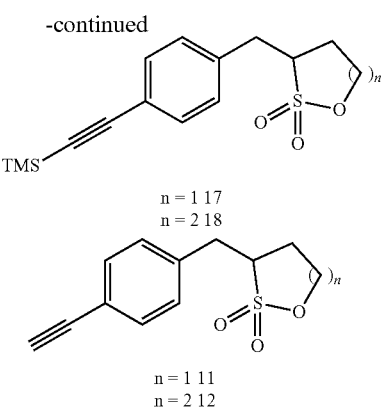

n = 1 17
n = 2 18

17 or 18 —m→

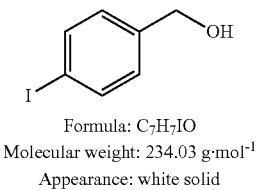

n = 1 11
n = 2 12

4-Iodobenzyl Alcohol 14 (Step i of Reaction Scheme 4)

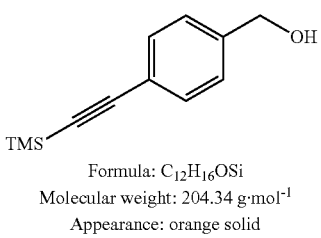 [SMILES: C[Si](C)(C)C#Cc1ccc(CO)cc1]

Formula: C₇H₇IO
Molecular weight: 234.03 g·mol⁻¹
Appearance: white solid

To a solution of 4-iodo-benzoic acid (3.00 g, 12.1 mmol, 1 equiv) in THF (20 mL) was added, drop by drop, a solution of the borane tetrahydrofuran complex (1M in THF, 23.1 mL, 242.0 mmol, 20 equiv). The mixture was mixed at ambient temperature for 24 h and treated with caution with 2N HCl. After extraction with DCM, the organic phases were washed with water, dried over MgSO₄ and concentrated under reduced pressure. Purification over silica gel with pentane/EtOAc 8:2 as eluent led to the desired compound 14 in the form of white solid (2.57 g, 91%).
CAS number: 18282-51-4

Spectroscopic data agree with those described by Yang et al, *Chem Eur J* 2011, 17, 5652-5660. pf: 69° C. (litt 71-73° C.). $R_f$: 0.15 (Pent/EtOAc 9:1). RMN ¹H (CDCl₃, 400 MHz): δ 4.65 (s, 2H), 7.11 (d, ³J=8.4 Hz, 2H), 7.69 (d, ³J=8.4 Hz, 2H). RMN ¹³C (CDCl₃, 100 MHz): δ 64.7, 93.0, 128.7, 137.6, 140.4. GCMS: calculated for C₇H₇IO: 234; found 234 (12.3 min).

(4-Trimethylsilanylethynyl-phenyl)-methanol 15
(step j of Reaction Scheme 4)

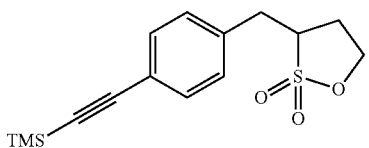

Formula: C₁₂H₁₆OSi
Molecular weight: 204.34 g·mol⁻¹
Appearance: orange solid

To a solution of (4-iodophenyl)-methanol 14 (0.70 g, 3.0 mmol, 1 equiv) in anhydrous 1,4-dioxane (10 mL) were added ethynyltrimethylsilane (0.5 mL, 3.6 mmol, 1.2 equiv), triethylamine (5.0 mL, 35.9 mmol, 12 equiv), copper iodide (57 mg, 0.30 mmol, 0.1 equiv) and bis(triphenylphosphine) palladium(II) dichloride (105 mg, 0.15 mmol, 0.05 equiv). The reaction medium was mixed at ambient temperature for 12 h, then filtered on celite. After addition of DCM, the organic phase was washed in water, dried over MgSO₄ and concentrated under reduced pressure. Purification on silica gel with pentane/EtOAc 9:1 as eluent led to the desired compound in the form of an orange solid (0.55 g, 90%).
CAS number: 275386-60-2

Spectroscopic data agree with those described in Hiraoka et al, *Angew Chem Int Ed* 2004, 43, 3814-3818. pf: 69° C. (litt 66° C.). $R_f$: 0.62 (Pent/EtOAC 9:1). RMN ¹H (CDCl₃, 400 MHz): δ 0.25 (s, 9H), 1.68 (s, 1H), 4.69 (s, 2H), 7.29 (d, ³J=7.7 Hz, 2H), 7.45 (d, ³J=7.7 Hz, 2H). RMN ¹³C (CDCl₃, 100 MHz): δ 0.0, 64.9, 94.2, 104.9, 122.4, 126.6, 132.2, 141.2. HRMS (ESI+): calculated for C₁₂H₁₆NaOSi: 227.0868 [M+Na]+; found: 227.0873. Elementary analysis: calculated for C₁₂H₁₆OSi: C, 70.53; H, 7.89. found C, 70.57; H, 8.75.

(4-Bromomethyl-phenylethynyl)-trimethyl-silane 16
(Step k of the Reaction Scheme 4)

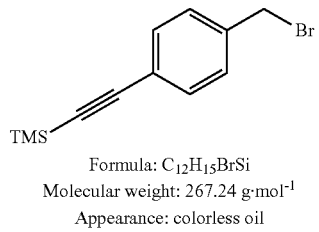 [SMILES: C[Si](C)(C)C#Cc1ccc(CBr)cc1]

Formula: C₁₂H₁₅BrSi
Molecular weight: 267.24 g·mol⁻¹
Appearance: colorless oil

To a solution of benzyl bromide 15 (0.30 g, 1.5 mmol, 1 equiv) in anhydrous Et₂O (10 mL) were added carbon tetrabromide (0.61 g, 1.8 mmol, 1.25 equiv) and triphenylphosphine (0.47 g, 1.8 mmol, 1.25 equiv). The mixture was mixed at ambient temperature for 4 h, filtered, and the filtrate was concentrated under reduced pressure. Purification on silica gel with heptane/EtOAc 8:2 as eluent led to the desired compound in the form of a colorless oil (325 mg, 84%).
CAS number: 686275-89-8

Spectroscopic data agree with those described by Leventis et al, *Chem Mater* 2004, 16, 1493-1506. $R_f$: 0.74 (Hetp/EtOAc 8:2). RMN ¹H (CDCl₃, 400 MHz): δ 0.25 (s, 9H), 4.45 (s, 2H), 7.31 (d, ³J=8.2 Hz, 2H), 7.42 (d, ³J=8.2 Hz, 2H). RMN ¹³C (CDCl₃, 100 MHz): δ 0.0, 32.9, 95.3, 104.5, 123.3, 128.9, 132.4, 138.0. GCMS: calculated for C₁₂H₁₅BrSi: 267; found: 266 (13.8 min).

[4-(2,2-Dioxo-[1,2]oxathiolan-3-ylmethyl)-phenylethynyl]-trimethyl-silane 17 (Step I of Reaction Scheme 4)

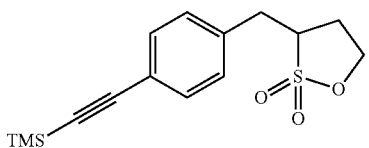

Formula: C₁₅H₂₀O₃SSi
Molecular weight: 308.47 g·mol⁻¹
Appearance: colorless oil

HMDS (1.55 mL, 7.65 mmol, 1.7 equiv) and anhydrous THF (10 mL) were introduced into a double-necked flask (A) under nitrogen. After being cooled to 0° C., n-butyl-lithium (1.6M in hexane, 4.8 mL, 7.65 mmol, 1.7 equiv) was added drop by drop. The mixture was mixed at 0° C. for 15 min, then at −78° C. for 10 min. Propane-1,3-sultone (820 mg, 6.7 mmol, 1.5 equiv), benzyl bromide 17 (1.20 g, 4.5 mmol, 1 equiv) and anhydrous THF (90 mL) were introduced into a second double-necked flask (B) under nitrogen. The mixture was cooled to −98° C. LiHMDS was transferred from flask A to flask B via a cannula and the final mixture was mixed at −98° C. for 4 h, allowed to reheat gently to 0° C. then treated with $H_2O$. After addition of EtOAc, the organic phase was washed in water, then in brine, dried over $MgSO_4$ and concentrated under reduced pressure. Purification on silica gel with heptane/EtOAc 1:1 as eluent led to the desired compound 17 in the form of a colorless oil (1.11 g, 80%). $R_f$: 0.14 (Pent/EtOAc 8:2). RMN $^1H$ (CDCl$_3$, 400 MHz): δ 0.08 (s, 9H), 2.14-2.17 (m, 1H), 2.29-2.32 (m, 1H), 2.68-2.74 (m, 1H), 3.14-3.19 (m, 1H), 3.31-3.35 (m, 1H), 4.15-4.27 (m, 2H), 7.02 (d, $^3J$=8.2 Hz, 2H), 7.27 (d, $^3J$=8.2 Hz, 2H). RMN $^{13}C$ (CDCl$_3$, 100 MHz): δ 0.05, 29.2, 34.5, 56.3, 66.9, 94.9, 104.5, 125.9, 128.8, 132.5, 136.4. HRMS (ESI+): calculated for $C_{15}H_{21}O_3SSi$: 309.0981 [M+H]+; found: 309.0995. MS/MS (ESI+): m/z (%) 309.2 (100) 155.1 (75).

3-(4-Ethynyl-benzyl)-[1,2]oxathiolone 2,2-dioxide 11 (Step m of Reaction Scheme 4)

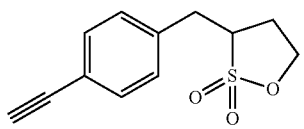

Formula: $C_{12}H_{12}O_3S$
Molecular weight: 236.29 g · mol$^{-1}$
Appearance: white solid To a solution of trimethylsilylsultone 17 (0.91 g, 2.9 mmol, 1 equiv) in THF (5 mL) was added, drop by drop at 0° C., TBAF (1M in THF, 0.30 mL, 0.30 mmol, 0.1 equiv). The mixture was mixed at 0° C. for 2 h. Purification on silica gel with heptane/Et$_2$O 1:1 as eluent and recrystallization at ambient temperature in petroleum ether led to the desired compound 11 in the form of a white solid (340 mg, 50%). mp: 118° C. $R_f$: 0.54 (pentane/Et$_2$O 1:1). RMN $^1H$ (CDCl$_3$, 400 MHz): δ 2.30-2.36 (m, 1H), 2.47-2.51 (m, 2H), 2.89 (dd, $^2J$=14.2 Hz, 3J=9.4 Hz, 1H), 3.09 (s, 1H), 3.38 (dd, $^2J$=14.2 Hz, $^3J$=5.7 Hz, 1H), 3.47-3.51 (m, 1H), 4.34 (dt, $^2J$=8.7 Hz, $^3J$=7.2 Hz, 1H), 4.43 (dt, $^2J$=8.8 Hz, $^{13}J$=3.8 Hz, 1H), 7.20 (dd, $^3J$=8.2 Hz, 2H), 7.46 (dd, $^3J$=8.2 Hz, 2H). RMN $^{13}C$ (CDCl$_3$, 100 MHz): δ 29.2, 34.5, 56.3, 66.8, 77.7, 121.4, 121.4, 128.9, 132.8, 136.3. HRMS (ESI$_+$): calculated for $C_{12}H_{13}O_3S$: 237.0585 [M+H]+; found: 237.0583.

2.3. Synthesis of Aromatic Acetylenic Sultone Precursors

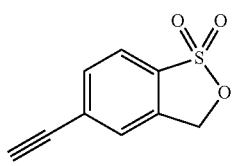

13

(Compound Corresponding to Formula (XX))
Reaction Scheme 5 was Followed:

Reaction scheme 5: Synthesis path of sultone 13

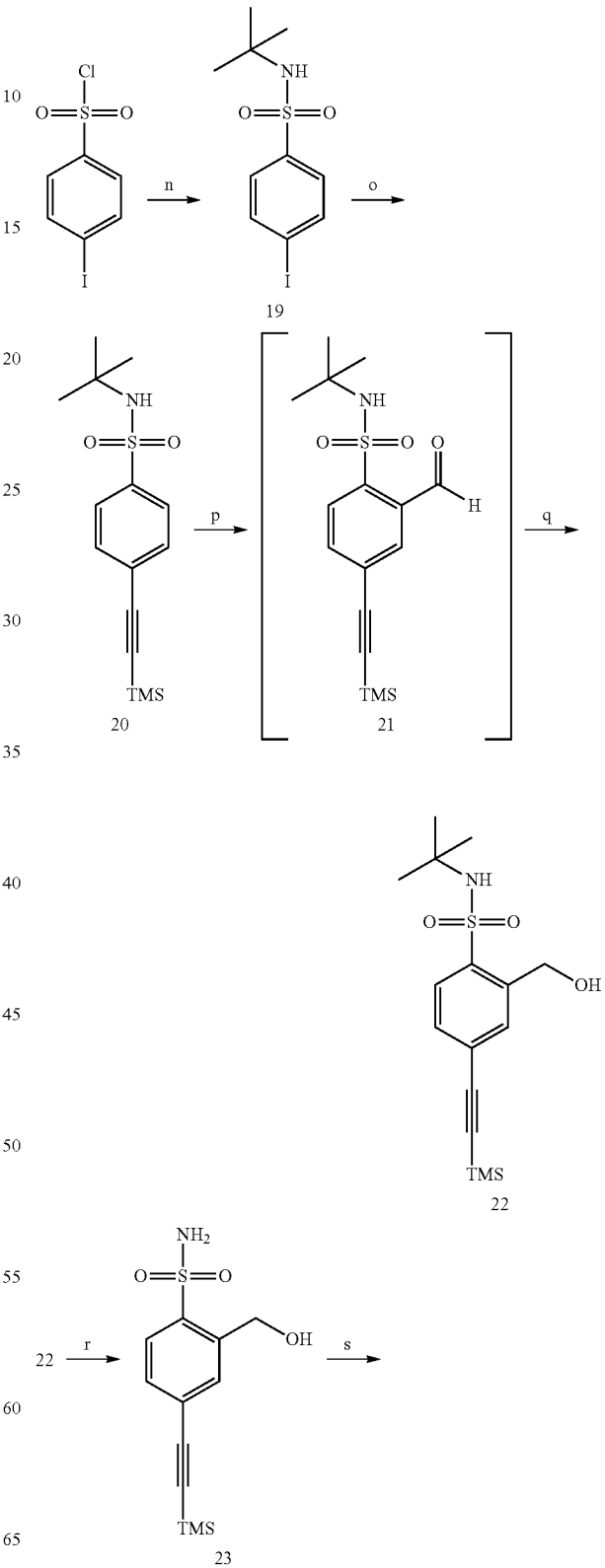

-continued

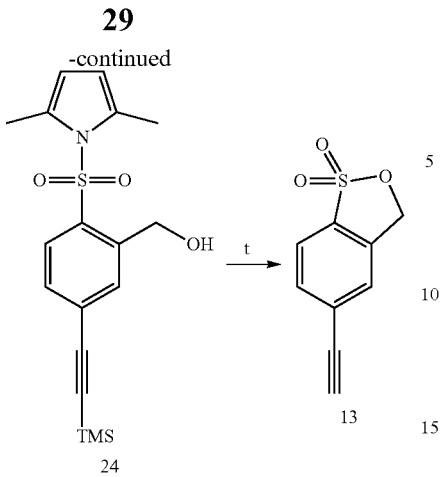

24

N-tert-Butyl-4-iodo-benzenesulfonamide 19 (Step n of Reaction Scheme 5)

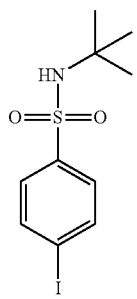

Formula: C₁₀H₁₄INO₂S
Molecular weight: 339.19 g·mol⁻¹
Appearance: white solid

To a solution of 4-iodophenylsulfonyl chloride (3.00 g, 9.9 mmol, 1 equiv) in anhydrous DCM (20 mL) was added triethylamine (2.1 mL, 14.9 mmol, 1.5 equiv). The mixture was cooled to 0° C. and tert-butylamine (1.6 mL, 14.9 mmol, 1.5 equiv) was added drop by drop. The mixture was mixed at 0° C. for 1 h, then at ambient temperature for 12 h and treated with 1N HCl. After extraction with DCM, the combined organic phases were washed with water, dried over MgSO₄ and concentrated under reduced pressure. Purification on silica gel with DCM as eluent led to the desired compound in the form of a white solid (3.31 g, 98%).

CAS number: 403793-15-7. pf: 137-138° C. RR: 0.50 (DCM). RMN ¹H (CDCl₃, 400 MHz): δ 1.20 (s, 9H), 5.23 (s, 1H), 7.61 (d, ³J=8.8 Hz, 2H), 7.82 (d, ³J=8.4 Hz, 2H). RMN ¹³C (CDCl₃, 100 MHz): δ 30.1, 54.9), 99.3, 128.4, 138.1, 143.3. IR (neat): ν 3251, 1567, 1326, 1146, 1008, 726, 612, 572. HRMS (ESI₊): calculated for C₁₀H₁₅INO₂S: 339.9868 [M+H]₊; found: 339.9878. MS/MS (ESI₊): m/z (%) 340.1 (27), 284.0 (100). Elementary analysis: calculated for C₁₀H₁₄INO₂S: C, 35.41; H, 4.16; N, 4.13; S, 9.45. found: C, 35.39; H, 4.02; N, 4.36; S, 9.94.

N-tert-Butyl-4-trimethylsilanylethynyl-benzene-sulfonamide 20 (Step o of Reaction Scheme 5)

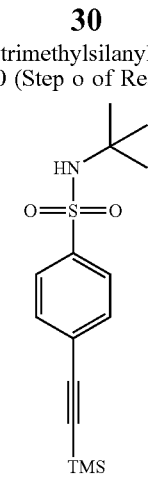

Formula: C₁₅H₂₃NO₂SSi
Molecular weight: 309.50 g·mol⁻¹
Appearance: orange solid

To a solution of sulfonamide 19 (2.00 g, 5.9 mmol, 1 equiv) in 1,4-dioxane (20 mL) were added ethynyltrimethylsilane (1.0 mL, 7.1 mmol, 1.2 equiv), trimethylamine (10.0 mL, 70.8 mmol, 12 equiv), copper iodide (112 mg, 0.59 mmol, 0.1 equiv) and bis(triphenylphosphine)palladium(II) dichloride (211 mg, 0.30 mmol, 0.05 equiv). The reaction medium was mixed at ambient temperature for 12 h then filtered over celite. After extraction with DCM, the combined organic phases were washed with water, dried over MgSO₄ and concentrated under reduced pressure. Purification on silica gel with pentane/EtOAc 9:1 as eluent led to the desired compound 20 in the form of an orange solid (1.73 g, 96%). pf: 147-148° C. R$_f$: 0.35 (Pent/EtOAc 9:1). RMN ¹H (CDCl₃, 400 MHz): δ 0.26 (s, 9H), 1.21 (s, 9H), 4.61 (s, 1H), 7.55 (dd, ³J=6.8 Hz, ⁴J=2.0 Hz, 2H), 7.81 (dd, ³J=6.8 Hz, ⁴J=2.0 Hz, 2H). RMN ¹³C (CDCl₃, 100 MHz): δ 0.0, 30.4, 55.0, 98.3, 103.5, 127.1, 127.5, 132.5, 143.0. IR (neat): ν 3253, 1436, 1324, 1147, 858, 601, 570. HRMS (ESI₊): calculated for C₁₅H₂₄NO₂SSi: 310.1297 [M+H]+; found: 310.1302. MS/MS (ESI₊): m/z (%) 310.2 (13) 254.1 (100) 237.1 (77). Elementary analysis: calculated for C₁₅H₂₃NO₂SSi: C, 58.21; H, 7.49; N, 4.53; S, 10.36. found: C, 57.8; H, 7.33; N, 4.61; S, 9.64.

N-tert-Butyl-2-hydroxymethyl-4-trimethylsilanyl-ethynyl benzenesulfonamide 22 (Steps p-q of Reaction Scheme 5)

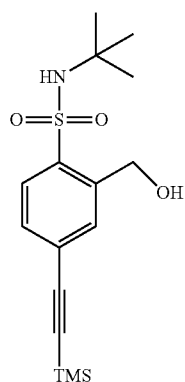

Formula: C₁₆H₂₅NO₃SSi
Molecular weight: 339.53 g·mol⁻¹
Appearance: white solid

To a solution of sulfonamide 20 (1.5 g, 4.9 mmol, 1 equiv) in anhydrous THF (10 mL) under nitrogen at −78° C. was added, drop by drop, a solution of n-butyllithium (1.6M in hexane, 9.1 mL, 14.6 mmol, 3 equiv). The mixture was mixed at −78° C. for 30 min, then at −20° C. for 15 min. After having been cooled to −78° C., anhydrous DMF (1.5 mL, 19.4 mmol, 4 equiv) was added drop by drop. The mixture was mixed at −78° C. for 4 h and allowed to reheat to ambient temperature for 12 h. The totality was transferred onto ammonium chloride cooled in ice. After extraction with EtOAc, the organic phase was dried over $MgSO_4$ and concentrated under reduced pressure. The oil obtained, containing aldehyde 21, was diluted in anhydrous THF (5 mL) and $NaBH_4$ (280 mg, 7.3 mmol, 1.5 equiv) was added by portions. The reaction medium was mixed at ambient temperature for 24 h and treated with $H_2O$ and extracted with EtOAc. The combined organic phases were washed with brine, dried over $MgSO_4$ and concentrated under reduced pressure. Purification on silica gel with pentane/EtOAc 7:3 as eluent led to the desired compound in the form of a white solid (681 mg, 41% in 2 steps). pf: 190-191° C. $R_f$: 0.50 (Pent/EtOAc 7:3). RMN $^1H$ ($CDCl_3$, 400 MHz): δ 0.26 (s, 9H), 1.22 (s, 9H), 1.57 (bs, 1H), 4.96 (s, 2H), 4.99 (bs, 1H), 7.49 (dd, 3=8.1 Hz, $^4J$=1.6 Hz, 1H), 7.60 (d, $^4J$=1.5 Hz, 1H), 7.96 (d, $^3J$=8.1 Hz, 1H). RMN $^{13}C$ ($CDCl_3$, 100 MHz): δ 0.0, 30.4, 55.5, 63.4, 98.7, 103.3, 128.1, 129.5, 131.6, 134.5, 138.6, 140.9. IR (neat): ν 3398, 2967, 1306, 1153, 830, 575. HRMS ($ESI_+$): calculated for $C_{16}H_{25}NNaO_3SSi$: 362.1215 [M+Na]+; found: 362.1222. Elementary analysis: calculated for $C_{16}H_{25}NO_3SSi$: C, 46.01; H, 5.79; N, 4.13; S, 9.45. found: C, 56.29; H, 7.31; N, 4.41; S, 10.06.

2-Hydroxymethyl-4-trimethylsilanylethynyl-benzenesulfonamide 23 (Step r of Reaction Scheme 5)

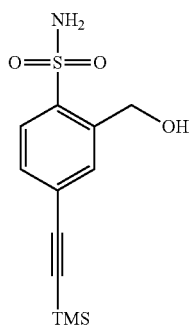

Formula: $C_{12}H_{17}NO_3SSi$
Molecular weight: 283.42 g.mol$^{-1}$
Appearance: white solid In a double-necked flask under nitrogen, to sulfonamide 22 (0.30 g, 0.88 mmol, 1 equiv) in anhydrous DCM anhydre (10 mL), was added, drop by drop, a solution of $BCl_3$ (1M in DCM, 0.97 mL, 0.97 mmol, 1.1 equiv). The reaction medium was mixed at ambient temperature for 1 h and treated with $H_2O$. After extraction with DCM, the combined organic phases were washed with brine, dried over $MgSO_4$ and concentrated under reduced pressure, which led to the desired compound 23 in the form of a white solid (129 mg, 52%). pf: 102° C. $R_f$: 0.43 (pentane/EtOAc 7:3). RMN $^1H$ ($CDCl_3$, 400 MHz): δ 0.26 (s, 9H), 4.97 (s, 2H), 7.48 (d, $^3J$=8.1 Hz, 1H), 7.51 (s, 1H), 7.92 (d, $^3J$=8.1 Hz, 1H). RMN $^{13}C$ ($CDCl_3$, 100 MHz): δ 0.0, 63.9, 99.1, 103.1, 128.4, 128.7, 132.1, 134.7, 137.9, 140.1. HRMS ($ESI_+$): calculated for $C_{12}H_{17}NNaO_3SSi$: 306.0596 [M+Na]+; found: 306.0612.

[2-(2,5-Dimethyl-pyrrole-1-sulfonyl)-5-trimethylsilanylethynyl-phenyl]-methanol 24 (Step s of Reaction Scheme 5)

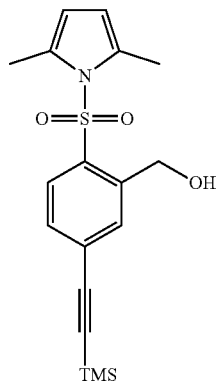

Formula: $C_{18}H_{23}NO_3SSi$
Molecular weight: 361.53 g · mol$^{-1}$
Appearance: yellow oil To a solution of sulfonamide 23 (104 mg, 0.37 mmol, 1 equiv) in anhydrous toluene (10 mL) were added 2,2,5,5-tetraethoxy-hexane (144 mg, 0.55 mmol, 1.5 equiv) and $P_2O_5$ (58 mg, 0.41 mmol, 1.1 equiv). The mixture was mixed under reflux for 2 h, cooled to ambient temperature and treated with 2M KOH (10 mL). After extraction with EtOAc, the combined organic phases were washed with water, dried over $MgSO_4$ and concentrated under reduced pressure. Purification on silica gel with a pentane/EtOAc 9:1 mixture as eluent led to the desired compound 24 in the form of a yellow oil (104 mg, 78%). $R_f$: 0.95 (Pent/EtOAc 7:3). RMN $^1H$ ($CDCl_3$, 400 MHz): δ 0.24 (s, 9H), 2.27 (s, 6H), 2.69 (bs, 1H), 4.88 (s, 2H), 5.92 (s, 2H), 6.74 (d, $^3J$=8.2 Hz, 1H), 7.35 (dd, $^3J$=8.2 Hz, $^4J$=1.5 Hz, 1H), 7.75 (d, $^4J$=1.1 Hz, 1H). RMN $^{13}C$ ($CDCl_3$, 100 MHz): δ 0.0, 15.7, 61.6, 99.6, 103.0, 112.1, 126.5, 129.1, 131.5, 133.6, 133.9, 138.5, 139.9. HRMS ($ESI_+$): calculated for $C_{18}H_{23}NNaO_3SSi$: 384.1066 [M+Na]+; found: 384.1072.

5-Ethynyl-3H-benzo[c][1,2]oxathiole 1,1-dioxide 13 (Step t of Reaction Scheme 5)

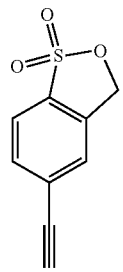

Formula: $C_9H_6O_3S$
Molecular weight: 194.21 g · mol$^{-1}$
Appearance: white solid To a solution of pyrrole 24 (400 mg, 1.1 mmol, 1 equiv) in anhydrous THF (5 mL) was added sodium hydride (59 mg, 2.4 mmol, 2.2 equiv) by portions. The mixture was mixed at ambient temperature for 12 h, then treated with H$_2$O. After extraction with EtOAc, the combined organic phases were washed with water, dried over MgSO$_{4a}$ and concentrated under reduced pressure. Purification on silica gel with pentane/Et$_2$O as eluent led to the desired compound 13 in the form of a colorless oil (68 mg, 32%). pf: 32° C. R$_f$: 0.46 (Pent/Et$_2$O 1:1). RMN $^1$H (CDCl$_3$, 400 MHz): δ 3.31 (s, 1H), 5.50 (s, 2H), 7.51 (bs, 1H), 7.68 (d, $^3$J=7.8 Hz, 1H), 7.79 (d, $^3$J=7.8 Hz, 1H). RMN 13C (CDCl$_3$, 100 MHz): δ 70.6, 81.2, 81.7, 122.0, 126.7, 128.2, 130.3, 133.7, 135.5.

HRMS (ESI$_+$): calculated for C$_9$H$_7$O$_3$S: 195.0116 [M+H].; found: 195.0117.

Example 3: Preparation of Compounds with Formula (XXI)

Radiofluorination of Acetylenic Sultones 3, 10-13 as [$^{18}$F] fluorosulfonates [$^{18}$F]5, [$^{18}$F]25-[$^{18}$F]28 (Step α) of the Method According to Alternative 2)

Sultones 3, 10-13 (5 mg) in ACN (500 μL) were added to the dried complex [$^{18}$F]KF/K$_{222}$ or to [$^{18}$F]TBAF and the sealed reaction chamber was heated to the desired temperature (ta, 50° C., 75° C. or 110° C.) for 15 min. Purification by HPLC led to the desired compound with radiochemical efficiencies of 80-95%.

| [$^{18}$F]-compounds | HPLC system and gradient | t$_R$ (min) | Precursor | t$_R$ (min) |
|---|---|---|---|---|
| [$^{18}$F]5 | C4 | 6.1 | 10 | 26.6 |
| [$^{18}$F]5 | B3 | 7.6 | 3 | 32.2 |
| [$^{18}$F]26 | B1 | 17.7 | 11 | 29.5 |
| [$^{18}$F]27 | B1 | 19.3 | 12 | 27.4 |
| [$^{18}$F]28 | B1 | 17.0 | 13 | 22.7 |

Synthesis of fluorosulfonates 5, 25-28 (Compounds Corresponding to Formula (XXI))

1-Fluoro-hex-5-yne-3-sulfonatetetrabutyl-ammonium 25

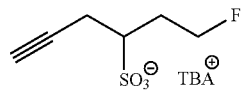

Formula: $C_{22}H_{44}FNO_3S$
Molecular weight: 421.65 g·mol$^{-1}$
Appearance: colorless oil To a solution of propargylic sultone 10 (100 mg, 0.63 mmol, 1 equiv) in anhydrous ACN (1 mL) was added TBAF (1M in THF, 0.69 mL, 0.69 mmol, 1.1 equiv). The mixture was mixed at ambient temperature for 12 h then concentrated under reduced pressure, which led to the desired compound in the form of a colorless oil (245 mg, 93%). RMN 1H (CD$_3$CN, 400 MHz): δ 0.86 (t, $^3$J=7.4 Hz, 12H), 1.21-1.31 (m, 8H), 1.47-1.55 (m, 8H), 1.98-2.09 (m, 2H), 2.16-2.24 (m, 2H), 2.53-2.60 (m, 1H), 2.70-2.76 (m, 1H), 3.03-3.07 (m, 8H), 4.51-4.71 (m, 2H). RMN 13C (CD$_3$CN, 100 MHz): δ 13.6, 20.1, 24.1, 31.7 (d, $^2$J$_{CF}$=20.4 Hz), 33.7, 55.2 (d, $^3$J$_{CF}$=6.2 Hz), 58.9, 70.8, 83.1, 83.4 (d, $^3$J$_{CF}$=159.5 Hz). RMN $^{18}$F (CD$_3$CN, 376 MHz): δ −217.3 (tt, $^2$J=47.3 Hz, $^3$J=22.0 Hz, 1F). HRMS (ESI-): calculated for C$_6$H$_8$FO$_3$S—: 179.0178 [M-H]−; found: 179.0171. MS/MS (ESI-): m/z (%) 179.0 (100) 159.0 (40) 81.0 (90).

7-Fluoro-hept-1-yne-4-sulfonatetetrabutyl-ammonium 5

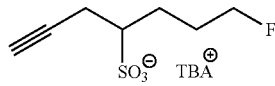

Formula: $C_{23}H_{46}FNO_3S$
Molecular weight: 435.68 g·mol$^{-1}$
Appearance: colorless oil To a solution of propargylic sultone 3 (100 mg, 0.57 mmol, 1 equiv) in anhydrous ACN (1 mL) was added TBAF (1M in THF, 0.63 mL, 0.63 mmol, 1.1 equiv). The mixture was mixed at ambient temperature for 12 h, then concentrated under reduced pressure, which led to the desired compound in the form of a colorless oil (225 mg, 90%). RMN $^1$H (CD$_3$CN, 400 MHz): δ 0.97 (t, $^3$J=7.4 Hz, 12H), 1.32-1.42 (m, 8H), 1.58-1.66 (m, 8H), 1.85-1.94 (m, 2H), 2.24-2.34 (m, 3H), 2.51-2.60 (m, 2H), 2.83 (dt, $^2$J=16.9 Hz, $^3$J=3.0 Hz, 2H), 3.14-3.19 (m, 8H), 4.37-4.52 (m, 2H). RMN $^{13}$C (CD$_3$CN, 100 MHz): δ 13.6, 20.1, 24.1, 26.5 (d, $^3$J$_{CF}$=5.8 Hz), 28.3, 28.8 (d, $^2$J$_{CF}$=19.1 Hz), 58.9, 72.9, 75.4, 83.4, 85.0 (d, $^1$J$_{CF}$=161.0 Hz). RMN $^{19}$F (CD$_3$CN, 376 MHz): δ −218.6 (tt, $^2$J=47.5 Hz, $^3$J=25.3 Hz, 1F). HRMS (ESI-): calculated for C$_7$H$_{10}$FO$_3$S—: 193.0335 [M-H]−; found: 193.0342. MS/MS (ESI-): m/z (%) 193.0 (20) 173.0 (10) 129.1 (5) 109.1 (4) 81.0 (100).

1-(4-Ethynylphenyl)-4-fluorobutane-2-sulfonate tetrabutylammonium 26

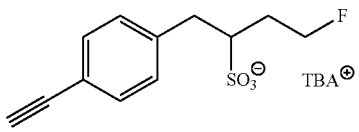

Formula: $C_{28}H_{48}FNO_3S$
Molecular weight: 497.33 g·mol$^{-1}$
Appearance: colorless oil To a solution of sultone 11 (50 mg, 0.21 mmol, 1 equiv) in anhydrous ACN (1 mL) was added TBAF (1M in THF, 0.23 mL, 0.23 mmol, 1.1 equiv). The mixture was mixed at ambient temperature for 12 h, then concentrated under reduced pressure, which led to the desired compound in the form of a colorless oil (50 mg, 92%). RMN $^1$H (CD$_3$CN, 400 MHz): δ 0.93 (t, $^3$J=7.2 Hz, 12H), 1.27-1.37 (m, 8H), 1.53-1.61 (m, 8H), 1.94-2.09 (m, 2H), 2.57 (dd, $^3$J=14.0 Hz, $^3$J=10.8 Hz, 2H), 2.75-2.81 (m, 2H), 3.07-3.11 (m, 8H), 3.39 (s, 1H), 4.38-4.59 (m, 2H), 7.22 (d, $^3$J=8.0 Hz, 2H), 7.36 (d, 3I=8.0 Hz, 2H). RMN $^{13}$C (CD$_3$CN, 100 MHz): δ 13.5, 20.0, 24.0, 31.4 (d, $^2$J$_{CF}$=21.0 Hz), 37.8, 57.6 (d, $^3$J$_{CF}$=6.0 Hz), 58.9, 78.3, 83.6 (d, $^1$J$_{CF}$=159.0 Hz), 83.9, 120.2, 130.1, 132.4, 142.5. RMN $^{19}$F (CD$_3$CN, 376 MHz): δ −216.7 (ddt, $^2$J=47.4 Hz, $^3$J=24.8 Hz, $^3$J=19.9 Hz). IR (neat): 2961, 2875, 2360, 1462, 1381, 1197, 1175, 1032, 731. HRMS (ESI-): calculated for C$_{12}$H$_{12}$FO$_3$S—: 255.0491 [M-H]−; found: 255.0497. MS/MS (ESI-): m/z (%) 255.1 (95) 235.0 (50) 205.0 (5) 141.1 (42) 81.0 (100).

Tetrabutylammonium 4-ethynyl-2-(fluoromethyl)benzenesulfonate 28

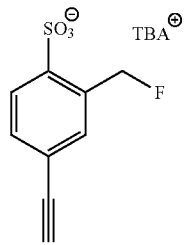

Formula: $C_{25}H_{42}FNO_3S$
Molecular weight: 455.67 g·mol$^{-1}$
Appearance: colorless oil To a solution of sultone 13 (22 mg, 0.11 mmol, 1 equiv) in 1 mL of anhydrous ACN (1 mL) was added TBAF (1M in THF, 0.13 mL, 0.13 mmol, 1.1 equiv). The reaction medium was mixed at ambient temperature for 24 h and concentrated, which led to the desired compound in the form of a colorless oil (48 mg, 93%). RMN $^1$H (CDCl$_3$, 400 MHz): δ 0.99 (t, $^3$J=7.3 Hz, 16H), 1.34-1.39 (m, 8H), 1.58-1.64 (m, 8H), 3.09-3.13 (m, 9H), 5.92 (d, $^2$J=47.9 Hz, 2H), 7.43 (d, $^3$J=8.0 Hz, 1H), 7.61 (s, 1H), 7.83 (d, $^3$J=7.9 Hz, 1H). RMN $^{13}$C (CDCl$_3$, 100 MHz): δ 58.8, 79.5, 82.2 (d, $^1$J$_{CF}$=163.5 Hz), 83.3, 123.2, 127.5, 129.3 (d, $^3$J$_{CF}$=13.9 Hz), 131.1 (d, $^4$J$_{CF}$=1.6 Hz), 135.8 (d, $^2$J$_{CF}$=17.4 Hz), 145.2 (d, $^3$J$_{CF}$=4.9 Hz). RMN $^{19}$F (CDCl$_3$, 376 MHz): δ −221.4 (t, $^2J_{1\text{-}F}$=47.9 Hz, 1F). HRMS (ESI−): calculated for: $C_9H_6FO_3S$—; 213.0022 [M−H]−; found: 213.0029. MS/MS (ESI−): m/z (%) 213.00 (100), 145.03 (30), 129.03 (22), 101.04 (20).

Example 4: Preparation of Compounds with Formula (I) (Step β) of the Method According to Alternative 2

By replacing the compound [$^{18}$F]5 by one of compounds [$^{18}$F]25-[$^{18}$F]28 prepared for example in step h of example 1.2. above, namely the reaction with azidomethylnitroimidazole 2, 3, on the compounds with respectively the following formulas 6, 7, 8 and 9 are obtained (which correspond to formula (I)):

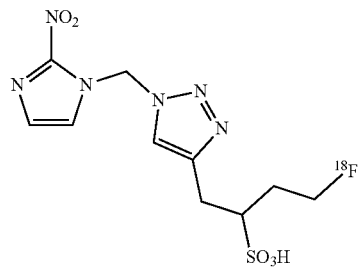

6

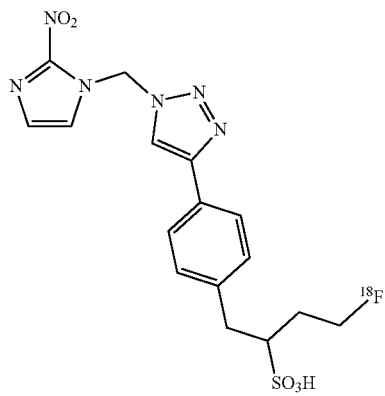

7

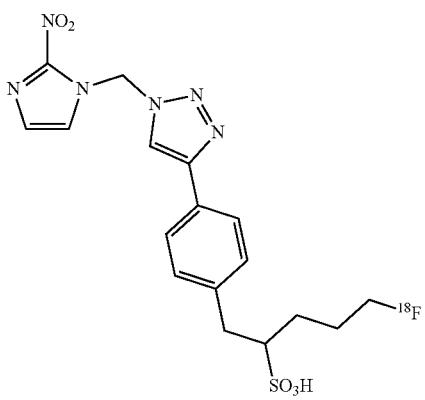

8

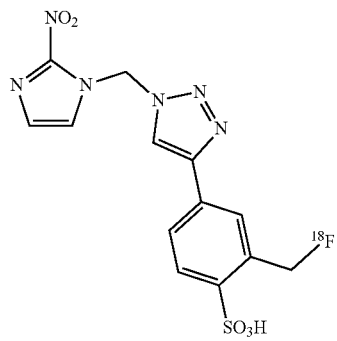

9

Example 5: Preparation of Compounds with Formula 1 According to Alternative 1 of the Reaction Scheme 3-((1-((2-Nitro-1H-imidazol-1-yl)methyl)-1H-1,2,3-triazol-4-yl)methyl)-1,2-oxathiolane 2,2-dioxide 30

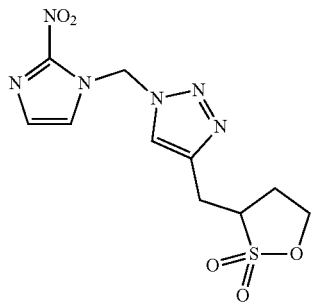

Formula: $C_{10}H_{12}N_6O_5S$
Molecular weight: 328.05 g·mol$^{-1}$
Appearance: white solid (Compound Corresponding to Formula (XI))

To a solution of azidoimidazole 2 (400 mg, 2.4 mmol, 1 equiv) in 1,4-dioxane (10 mL) were added acetylenic sultone 10 (387 mg, 2.4 mmol, 1 equiv), copper iodide (46 mg, 0.24 mmol, 0.1 equiv) and triethylamine (100 μL, 0.24 mmol, 0.1 equiv). The reaction medium was mixed at ambient temperature for 24 h, then separated between EtOAc and $H_2O$. After separation, the organic phase was washed with $H_2O$ and brine, dried over $MgSO_4$ and concentrated under reduced pressure. Purification on silica gel with DCM/MeOH 9:1 as eluent led to the desired compound 30 in the form of a white solid (680 mg, 84%). pf: 98° C. $R_f$: 0.38 (DCM/MeOH 9:1). RMN $^1H$ (CDCl$_3$, 400 MHz): δ 1.80-2.20 (m, 2H), 3.00 (dd, $^2J$=15.1 Hz, $^3J$=7.8 Hz, 1H), 3.40 (dd, $^2J$=15.1 Hz, $^3J$=5.8 Hz, 1H), 3.48-3.50 (m, 1H), 4.45-4.57 (m, 2H), 6.81-6.89 (m, 2H), 7.19 (s, 1H), 7.44 (s, 1H), 7.93 (s, 1H). RMN $^{13}C$ (CDCl$_3$, 100 MHz): δ 23.7, 29.5, 57.8, 59.2, 74.7, 123.8, 126.7, 129.9, 143.1, 144.9. RMN $^{15}N$ (CDCl$_3$, 50 MHz): δ 166.6, 240.5, 269.7, 359.1, 363.4. HRMS (ESI+): calculated for $C_{11}H_{15}N_6OsS$: 328.0590 [M+H]+; found: 328.0578.

3-((1-((2-Nitro-1H-imidazol-1-yl)methyl)-1H-1,2,3-triazol-4-yl)phenylmethyl)-1,2-oxathiolane 2,2-dioxide 31

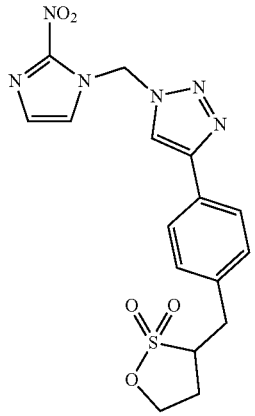

Formula: $C_{16}H_{16}N_6O_5S$
Molecular weight: 404.09 g·mol$^{-1}$
Appearance: white solid (Compound Corresponding to Formula (XI))

To a solution of azidoimidazole 2 (400 mg, 2.4 mmol, 1 equiv) in 1,4-dioxane (10 mL) were added acetylenic sultone 11 (566 mg, 2.4 mmol, 1 equiv), copper iodide (46 mg, 0.24 mmol, 0.1 equiv) and triethylamine (100 µL, 0.24 mmol, 0.1 equiv). The reaction medium was mixed at ambient temperature for 24 h then separated between EtOAc and H$_2$O. After separation, the organic phase was washed with H$_2$O and brine, dried over MgSO$_4$ and concentrated under reduced pressure. Purification on silica gel with DCM/MeOH 9:1 as eluent led to the desired compound 31 in the form of a white solid (680 mg, 84%). pf: 145° C. R$_f$: 0.48 (DCM/MeOH 9:1). RMN $^1$H (CDCl$_3$, 400 MHz): δ 1.80-2.20 (m, 2H), 3.00 (dd, $^2$J=15.1 Hz, $^3$J=7.8 Hz, 1H), 3.40 (dd, $^2$J=15.1 Hz, $^3$J=5.8 Hz, 1H), 3.48-3.50 (m, 1H), 4.45-4.57 (m, 2H), 6.81-6.89 (m, 2H), 7.19-7.98 (m, 7H). RMN $^{13}$C (CDCl$_3$, 100 MHz): δ 23.7, 29.5, 57.8, 59.2, 74.7, 123.8, 126.7, 129.9, 130.2, 133.4, 137.8, 139.2, 143.1, 144.9. RMN $^{15}$N (CDCl$_3$, 50 MHz): δ 166.6, 240.5, 269.7, 359.1, 363.4. HRMS (ESI$_+$): calculated for $C_{11}H_{15}N_6O_5S$: 404.0903 [M+H]$_+$; found: 404.0908.

3-((1-((2-Nitro-1H-imidazol-1-yl)methyl)-1H-1,2,3-triazol-4-yl)-4-yl)phenylmethyl)-1,2-oxathiane 2,2-dioxide 32

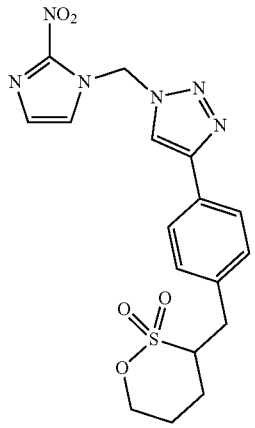

Formula: $C_{17}H_{18}N_6O_5S$
Molecular weight: 418.10 g·mol$^{-1}$
Appearance: white solid (Compound Corresponding to Formula (XI))

To a solution of azidoimidazole 2 (400 mg, 2.4 mmol, 1 equiv) in 1,4-dioxane (10 mL) were added acetylenic sultone 12 (600 mg, 2.4 mmol, 1 equiv), copper iodide (46 mg, 0.24 mmol, 0.1 equiv) and triethylamine (100 µL, 0.24 mmol, 0.1 equiv). The reaction medium was mixed at ambient temperature for 24 h, then separated between EtOAc and H$_2$O. After separation, the organic phase was washed with H$_2$O and brine, dried over MgSO$_4$ and concentrated under reduced pressure. Purification on silica gel with DCM/MeOH 9:1 as eluent led to the desired compound 32 in the form of a white solid (680 mg, 84%). pf: 154° C. R$_f$: 0.49 (DCM/MeOH 9:1). RMN $^1$H (CDCl$_3$, 400 MHz): δ 1.80-2.20 (m, 4H), 3.00 (dd, $^2$J=15.1 Hz, $^3$J=7.8 Hz, 1H), 3.40 (dd, $^2$J=15.1 Hz, $^3$J=5.8 Hz, 1H), 3.48-3.50 (m, 1H), 4.45-4.57 (m, 2H), 6.81-6.89 (m, 2H), 7.10-7.95 (m, 7H). RMN $^{13}$C (CDCl$_3$, 100 MHz): δ 23.7, 29.5, 57.8, 59.2, 74.7, 123.8, 126.7, 129.9, 130.2, 133.4, 137.8, 139.2, 143.1, 144.9. RMN $^{15}$N (CDCl$_3$, 50 MHz): δ 166.6, 240.5, 269.7, 359.1, 363.4. HRMS (ESI$_+$): calculated for $C_{11}H_{15}N_6O_5S$: 418.1059 [M+H]+; found: 418.1045.

Synthesis of 6 and [$^{18}$F]6:

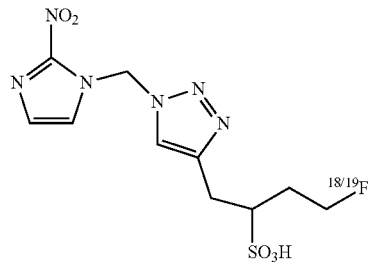

The precursor sultone 30 (15 mg) in ACN (500 µL) was added to the dried complex [$^{18/19}$F]KF/K$_{222}$ (or [$^{18/19}$F]TBAF) and the sealed reaction chamber was heated to 110° C. for 15 min. Purification by HPLC led to the desired compound with radiochemical (or chemical) efficiencies of 80-95%. HPLC: System B, gradient 3. 6 or [$^{18}$F]6 (t$_R$=23.1 min), precursor sultone 30 (t$_R$=34.4 min).

Synthesis of 7 [$^{18}$F]7:

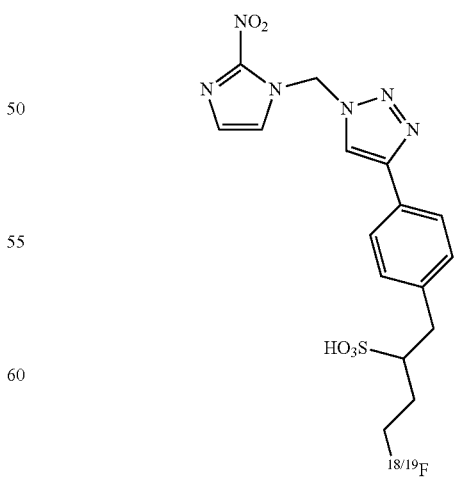

The precursor sultone 31 (15 mg) in ACN (500 µL) was added to the dried complex [$^{18/19F}$]KF/K$_{222}$ (or [$^{18/19}$F]

TBAF) and the sealed reaction chamber was heated to 110° C. for 15 min. Purification by HPLC led to the desired compound with radiochemical (or chemical) efficiencies of 80-95%. HPLC: System B, gradient 3. 7 or [$^{18}$F]7 ($t_R$=25.1 min), precursor sultone 31 ($t_R$=29.4 min).

Synthesis of 8 and [$^{18}$F]8:

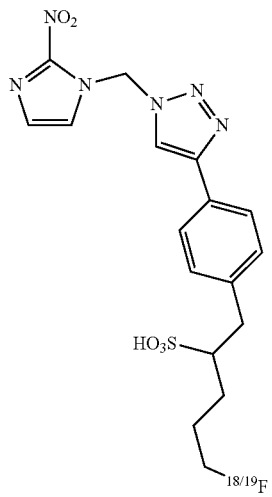

The precursor sultone 32 (15 mg) in ACN (500 μL) was added to the dried complex [18/19F]KF/K$_{222}$ (or [18/19F]TBAF) and the sealed reaction chamber was heated to 110° C. for 15 min. Purification by HPLC led to the desired compound with radiochemical (or chemical) efficiencies of 80-95%. HPLC: System B, gradient 3. 7 or [$^{18}$F]6 ($t_R$=27.2 min), precursor sultone 32 ($t_R$=31.4 min).

Example 6: Results of In Vivo Evaluations

Comparison of Radioligand [$^{18}$F]AEL-3156 with [$^{18}$F]MISO:

The animals were imaged for 180 consecutive minutes starting with the injection of the radiotracer [$^{18}$F]AEL-3156 (23±3 MBq) or [$^{18}$F]FMISO (18±3 MBq) coinciding with the beginning of TEP acquisition. The 180 min post-injection time is known to be optimal for this animal model, for obtaining imaging of hypoxia with TEP tracers such as [$^{18}$F]FMISO and [$^{18}$F]HX4. After TEP imaging and before waking, the animals systematically received an intraperitoneal injection of saline solution (2 mL) in order to rehydrate them.

The results obtained, provided in tables 1 and 2 below, show, at 20-30 min of acquisition:

an optimal tumor to muscle ratio (of 3 in $SUV_{mean}$ or of 5 in $SUV_{max}$) for [$^{18}$F]AEL-3156 et 3 times lower (1 in $SUV_{mean}$ or 1.7 in $SUV_{max}$) for [$^{18}$F]FMISO.

For [$^{18}$F]AEL-3156, the optimal ratio remains constant at least 60 min post-injection.

For [$^{18}$F]FMISO, this optimal ratio is achieved only after 180 minutes of acquisition.

TABLE 1

| $SUV_{Mean}$ of [$^{18}$F]AEL-3156 and of [$^{18}$F] FMISO as a function of time | | | | |
|---|---|---|---|---|
| | [$^{18}$F]AEL-3156 (according to the invention) | | [$^{18}$F] FMISO (for comparison) | |
| $SUV_{Mean}$ | average | standard deviation | average | standard deviation |
| 20-30 min | 2.94 | 0.37 | 1.00 | — |
| 40-60 min | 2.93 | 0.65 | 1.45 | — |
| 160-180 min | 1.51 | 0.83 | 3.42 | 0.12 |
| $SUV_{Max}$ of [$^{18}$F]AEL-3156 and of [$^{18}$F] FMISO as a function of time | | | | |
| | [$^{18}$F]AEL-3156 (according to the invention) | | [$^{18}$F] FMISO (for comparison) | |
| $SUV_{Max}$ | average | standard deviation | average | standard deviation |
| 20-30 min | 5.20 | 0.59 | 2.04 | — |
| 40-60 min | 5.10 | 0.84 | 3.64 | — |
| 160-180 min | 2.90 | 1.06 | 5.42 | 0.90 |

The invention claimed is:

1. A compound with the following formula (I):

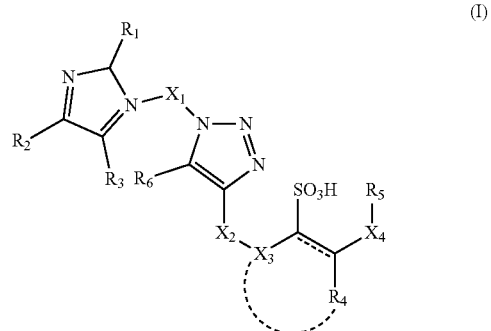

wherein:

$R_1$ represents $NO_2$, $R_2$ and $R_3$ represent —H, $X_1$ represents an alkylene comprising from 1 to 4 carbon atoms, possibly interrupted by a group selected from —O—, —S—, —(C=O)—, —(CONR$_{14}$)—, —(NR$_{15}$CO)—, —NR$_{16}$R$_{17}$—, a cycloalkylene of 3 to 8 atoms and a heterocycloalkylene of 3 to 8 atoms, said cycloalkylene and heterocycloalkylene being possibly substituted by one or more groups selected from —S(O)$_m$R$_{18}$ where m represents an integer from 0 to 2, —R$_{19}$, —OR$_{20}$, —NR$_{21}$R$_{22}$ and a halogen, $X_2$ represents a single bond or an arylene comprising from 5 to 6 atoms, and possibly substituted by one or more groups selected from —COR$_{23}$, —COOR$_{24}$, —CONR$_{25}$R$_{26}$, —NR$_{27}$R$_{28}$, —S(O)pR$_{29}$ where p represents an integer from 0 to 2, —R$_{30}$, —OR$_{31}$, a halogen, a cycloalkyl of 3 to 8 atoms and heterocycloalkyl of 3 to 8 members, said cycloalkylene and heterocycloalkylene possibly being substituted by one or more groups selected from the groups —S(O)$_q$R$_{41}$ where q represents an integer from 0 to 2, —R$_{42}$, —OR$_{43}$, —NR$_{44}$R$_{45}$ and a halogen, $X_3$ represents a multivalent hydrocarbon chain comprising from 1 to 6 carbon atoms, possibly interrupted by a group selected from —O—, —S—, —C(=O)—, —(CONR$_{32}$)—, —(NR$_{33}$CO)—, —NR$_{34}$R$_{35}$—, a cycloalkylene or heterocycloalkylene of 3 to 8 atoms, said cycloalkylene and heterocycloalkylene possibly being substituted by one or more groups selected among —S(O)nR$_{36}$ where n represents an integer from 0 to 2, —R$_{37}$, —OR$_{38}$, —NR$_{39}$R$_{40}$ and a halogen, R$_4$ represents —H, —OR$_{12}$ or a halogen, or R$_4$ and X$_3$ are bonded together to form a phenyl with the carbon atoms that carry them, X$_4$ represents —CR$_7$R$_8$— or —CR$_7$R$_8$—CR$_9$R$_{10}$—, R$_5$, R$_6$, R$_7$, R$_8$, R$_9$ and R$_{10}$ represent independently —H, —OR$_{13}$, a halogen or a radionuclide, provided that at least one of R$_5$, R$_6$, R$_7$, R$_8$, R$_9$ and R$_{10}$ represents a radionuclide, R$_{11}$, R$_{12}$, R$_{13}$, R$_{14}$, R$_{15}$, R$_{16}$, R$_{17}$, R$_{18}$, R$_{20}$, R$_{21}$, R$_{22}$, R$_{23}$, R$_{24}$, R$_{25}$, R$_{26}$, R$_{27}$, R$_{28}$, R$_{29}$, R$_{31}$, R$_{32}$, R$_{33}$, R$_{34}$, R$_{35}$, R$_{36}$, R$_{38}$, R$_{39}$, R$_{40}$, R$_{41}$, R$_{43}$, R$_{44}$ and R$_{45}$ represent independently H or a linear, branched or cyclic alkyl, comprising from 1 to 4 carbon atoms, R$_{19}$, R$_{30}$, R$_{37}$, and R$_{42}$ represent independently a linear, branched or cyclic alkyl comprising from 1 to 4 carbon atoms, or one of its pharmaceutically acceptable salts.

2. The compound according to claim 1, with the following formula (II):

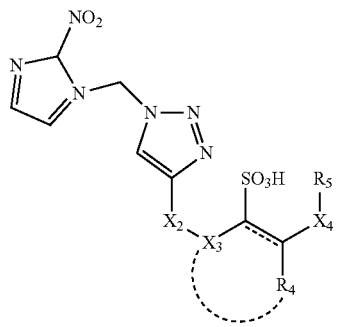

wherein X2, X3, X4, R4, and R5 are as defined in claim 1.

3. The compound according to claim 2, with the following formula (IIIa), (IIIb), (IIIc), (IIId) or (IV):

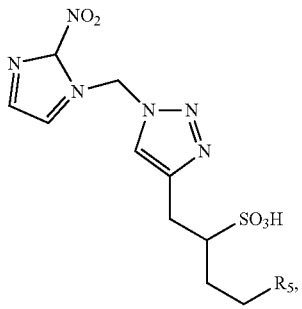
(IIIa)

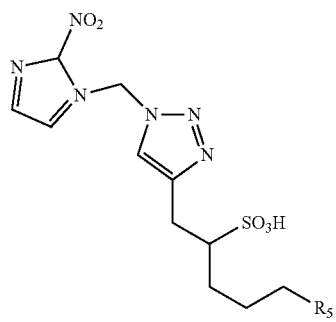
(IIIb)

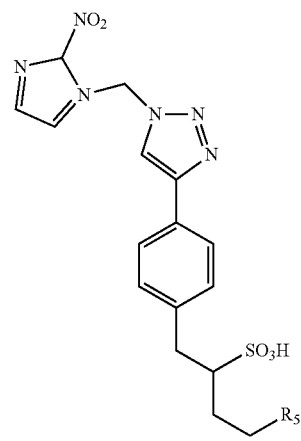
(IIIc)

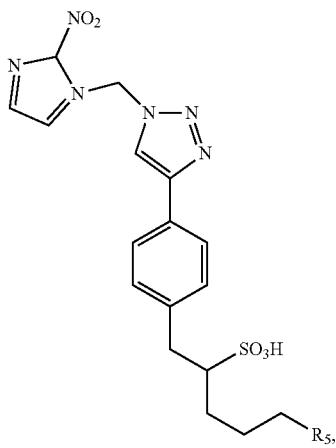
(IIId)

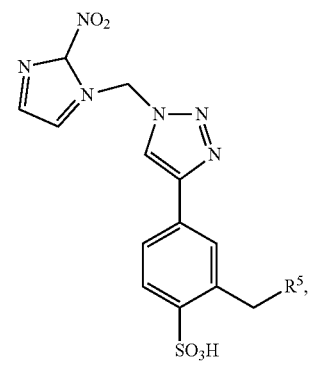
(IV)

wherein R$_5$ is a radionuclide.

4. A method for preparing the compound according to claim 1, comprising a step b) of reaction of a radionuclide and a compound with the following formula (XI):

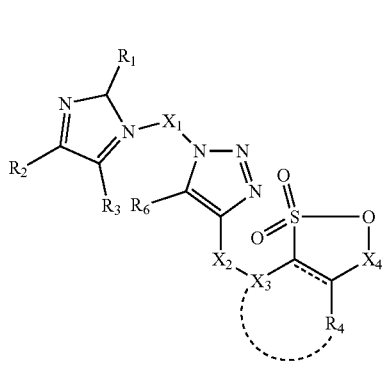

(XI)

wherein $R_1$, $R_2$, $R_3$, $X_1$, $X_2$, $X_3$, $X_4$, $R_4$ and $R_6$ are as defined in claim 1.

5. The method according to claim 4, comprising, prior to step b), a step a) consisting of preparing the compound with formula (XI) comprising the reaction of a compound with the following formula (X):

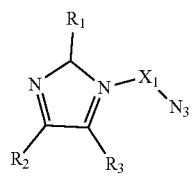

(X)

wherein $R_1$, $R_2$, $R_3$, and $X_1$ are as defined in claim 1, with a compound having the following formula (XX):

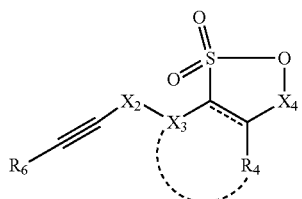

(XX)

wherein $X_2$, $X_3$, $X_4$, $R_4$ and $R_6$ are as defined in claim 1.

6. The method for preparing the compound according to claim 1, comprising a step β) of reaction of a compound with the following formula (X):

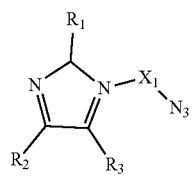

(X)

wherein $R_1$, $R_2$, $R_3$, and $X_1$ are as defined in claim 1, with a compound having the following formula (XXI):

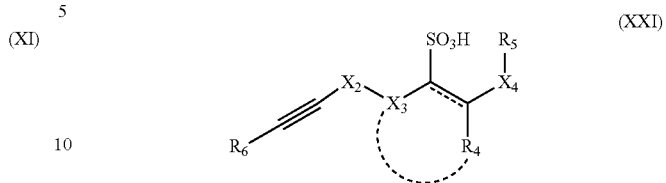

(XXI)

wherein $X_2$, $X_3$, $X_4$, $R_4$, $R_5$ and $R_6$ are as defined in claim 1.

7. The method according to claim 6 comprising, prior to step β), a step α) of preparation of the compound with formula (XXI) comprising the reaction of a radionuclide with a compound with the following formula (XX):

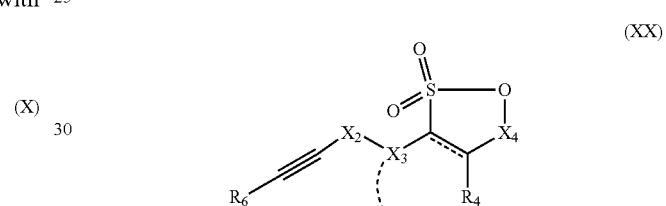

(XX)

wherein $X_2$, $X_3$, $X_4$, $R_4$ and $R_6$ are as defined in claim 1.

8. A compound with the following formula (XX), (XI) or (XXI), in the form of a base or of a salt:

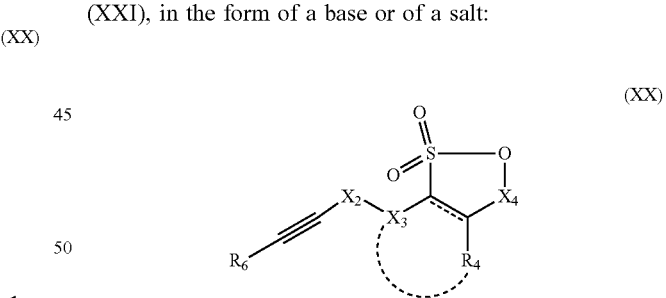

(XX)

wherein $X_2$, $X_3$, $X_4$, $R_4$ and $R_6$ are as defined in claim 1,

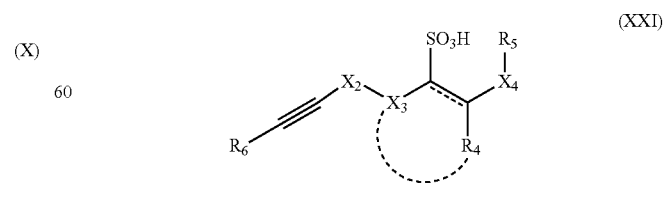

(XXI)

wherein $X_2$, $X_3$, $X_4$, $R_4$, $R_5$ and $R_6$ are as defined in claim 1, or

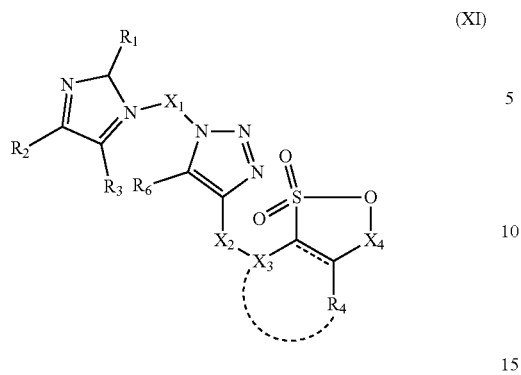

(XI)

wherein $R_1$, $R_2$, $R_3$, $X_1$, $X_2$, $X_3$, $X_4$, $R_4$ and $R_6$ are as defined in claim 1.

9. An imaging agent, particularly for positron emission tomography, comprising a compound of claim 1, or one of its pharmaceutically acceptable salts.

10. An in vivo diagnostic method for detecting hypoxia or a disease associated with hypoxia in a subject, the method comprising administering to the subject an effective amount of a compound of the Formula (I) in claim 1, and detecting the presence of the radionuclide in hypoxic cells of the subject by positron emission tomography.

11. A compound according to claim 1 or one of its pharmaceutically acceptable salts, wherein $R_5$ is $^{18}F$.

12. The method of claim 10, wherein the disease associated with hypoxia is selected from the group consisting of cancer, heart disease, ischemic disease, vascular disease, a stroke, and cerebral vascular accident.

* * * * *